(12) United States Patent
Starcevic et al.

(10) Patent No.: US 9,388,188 B2
(45) Date of Patent: *Jul. 12, 2016

(54) SYNTHETIC ROUTE FOR THE PREPARATION OF β-AMINOBUTYRYL SUBSTITUTED 5,6,7,8-TETRAHYDRO[1,4]DIAZOLO[4,3-ALPHA]PYRAZIN-7-YL COMPOUNDS

(71) Applicant: Lek Pharmaceuticals d.d., Ljubljana (SI)

(72) Inventors: Stefan Starcevic, Ljubljana (SI); Peter Mrak, Ljubljana (SI); Gregor Kopitar, Ljubljana (SI)

(73) Assignee: Lek Pharmaceuticals d.d. (SI)

( * ) Notice: Subject to any disclaimer, the term of this patent is extended or adjusted under 35 U.S.C. 154(b) by 0 days.

This patent is subject to a terminal disclaimer.

(21) Appl. No.: 14/406,686

(22) PCT Filed: Jun. 13, 2013

(86) PCT No.: PCT/EP2013/062307
§ 371 (c)(1),
(2) Date: Dec. 9, 2014

(87) PCT Pub. No.: WO2013/186326
PCT Pub. Date: Dec. 19, 2013

(65) Prior Publication Data
US 2015/0148533 A1    May 28, 2015

(30) Foreign Application Priority Data
Jun. 14, 2012 (EP) .................................. 12172012

(51) Int. Cl.
*C07D 487/04* (2006.01)
*C07D 205/08* (2006.01)
*C07C 227/18* (2006.01)

(52) U.S. Cl.
CPC ............ *C07D 487/04* (2013.01); *C07C 227/18* (2013.01); *C07D 205/08* (2013.01)

(58) Field of Classification Search
CPC .. C07D 487/04; C07D 487/14; C07D 205/08; C07C 277/16; C07C 277/18
See application file for complete search history.

(56) References Cited

FOREIGN PATENT DOCUMENTS

| CN | 102093245 A | 6/2011 | |
|---|---|---|---|
| CN | 102126976 A | 7/2011 | |
| EP | 2397141 A1 | 12/2011 | |
| ES | 2335380 A1 | 3/2010 | |
| IN | WO 2012025944 A2 * | 3/2012 | .......... C07D 487/04 |
| WO | 03004498 A1 | 1/2003 | |
| WO | 2004085378 A1 | 10/2004 | |
| WO | 2004085661 A2 | 10/2004 | |
| WO | 2004087650 A2 | 10/2004 | |
| WO | 2004089362 A1 | 10/2004 | |
| WO | 2005097733 A1 | 10/2005 | |
| WO | 2006081151 A1 | 8/2006 | |
| WO | 2008019124 A1 | 2/2008 | |
| WO | 2009045507 A2 | 4/2009 | |
| WO | 2009064476 A1 | 5/2009 | |
| WO | 2009084024 A2 | 7/2009 | |
| WO | 2009085990 A2 | 7/2009 | |
| WO | 2010122578 A2 | 10/2010 | |
| WO | 20100131025 A1 | 11/2010 | |
| WO | 2011025932 A2 | 3/2011 | |
| WO | 2011035725 A1 | 3/2011 | |
| WO | 2011060213 A2 | 5/2011 | |
| WO | 2011113399 A1 | 9/2011 | |
| WO | 2011116686 A1 | 9/2011 | |
| WO | 2011127794 A1 | 10/2011 | |
| WO | 2011142825 A2 | 11/2011 | |

OTHER PUBLICATIONS

Anon. IP.com Journal (2008), 8(12A), 8 (No. IPCOM000176671D, Nov. 20, 2009) (STN abstract and reactions attached).*
Tasnadi, Gabor, et al., Candida antarctica lipase B-catalyzed ring opening of 4-arylalkyl-substituted beta-lactams, Tetrahedron Asymmetry, Nov. 26, 2007, pp. 2841-2844, vol. 18, No. 23, Pergamon Press Ltd., Oxford, GB.
Yoakim, Christiane, et al., Beta-lactam derivatives as inhibitors of human cytomegalovirus protease, Journal of Medicinal Chemistry, Jul. 1, 1998, pp. 2882-2891, vol. 41, No. 15.
Hansen, Karl B., et al., First generation process for the preparation of the DPP-IV inhibitor sitagliptin, Organic Process Research & Development, Sep. 1, 2005, pp. 634-639, vol. 9, No. 5, American Chemical Society, US.
Kubryk, Michele, et al., Application of the asymmetric hydrogenation of enamines to the preparation of a beta-amino acid pharmacophore, Tetrahedron Asymmetry, Jan. 23, 2006, pp. 205-209, vol. 17, No. 2, Pergamon Press Ltd., Oxford, GB.

* cited by examiner

*Primary Examiner* — Golam M M Shameem
*Assistant Examiner* — Laura Daniel
(74) *Attorney, Agent, or Firm* — Luedeka Neely Group, P.C.

(57) ABSTRACT

The present invention relates to a process for preparing ☐-aminobutyryl substituted 5,6,7,8-tetrahydro[1,4]diazolo[4,3-α]pyrazin-7-yl compounds.

11 Claims, No Drawings

SYNTHETIC ROUTE FOR THE PREPARATION OF β-AMINOBUTYRYL SUBSTITUTED 5,6,7,8-TETRAHYDRO[1,4] DIAZOLO[4,3-ALPHA]PYRAZIN-7-YL COMPOUNDS

This application is a national phase entry of PCT International application number PCT/EP2013/062307, filed Jun. 13, 2013. This application also claims the benefit of the earlier filing date of: (1) EP 12172012.2, filed Jun. 14, 2012.

FIELD OF THE INVENTION

The present invention relates to the field of organic chemistry, more specifically to a process for preparing β-aminobutyryl substituted 5,6,7,8-tetrahydro[1,4]diazolo[4,3-α]pyrazin-7-yl compounds. Such compounds are useful as key structure framework of modern drug chemistry and especially of antidiabetic agents.

BACKGROUND OF THE INVENTION

β-Amino acids are of interest in the preparation of active pharmaceutical ingredients (APIs). The β-amino acid moiety in APIs of interest is normally part of a complex whole structure. Complexity is typically enhanced when considering a chiral center at the β-position of the β-aminobutyryl group and the general desire to obtain enantiopure compounds.

A particularly interesting class of APIs having β-amino acid structural moieties are dipeptidyl peptidase-4 (DPP-4) inhibitors which act as antidiabetic agents. DPP-4 inhibitors are oral antidiabetic drugs which reduce glucose blood levels by a new mechanism of action in which the DPP-4 inhibitors ("gliptins") inhibit inactivation of glucagon-like peptide (GLP), which stimulate insulin secretion. The benefit of these medicines lies in their lower side-effects (e.g., less hypoglycemia, less weight gain) and in the control of blood glucose values. It can be used for treatment of diabetes mellitus type 2.

The first member of the novel pharmacological group is sitagliptin which is chemically (R)-3-amino-1-(3-(trifluoromethyl)-5,6-dihydro-[1,2,4]triazolo[4,3-a]pyrazin-7(8H)-yl)-4-(2,4,5-trifluorophenyl)butan-1-one and which has the following structural formula

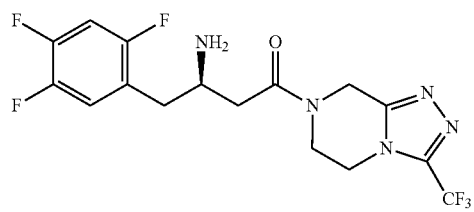 [SMILES: N[C@@H](CC(=O)N1CCn2c(nnc2C(F)(F)F)C1)Cc1cc(F)c(F)cc1F]

including a β-amino acid part.

However, an inclusion of a β-amino acid framework into a more complex molecule remains a permanent challenge for industrial production.

This is well reflected in the literature for the synthesis of sitagliptin. Several methods are described how to introduce the β-amino acid structure into the molecule of sitagliptin. The first synthesis of sitagliptin molecule disclosed in WO 03/004498 uses an unusual chiral dihydropyrazine promoter, diazomethane and silver salts, which compounds are unacceptable reagents for industrial synthesis. The synthetic pathway of WO 03/004498 is depicted in Scheme 1.

Scheme 1

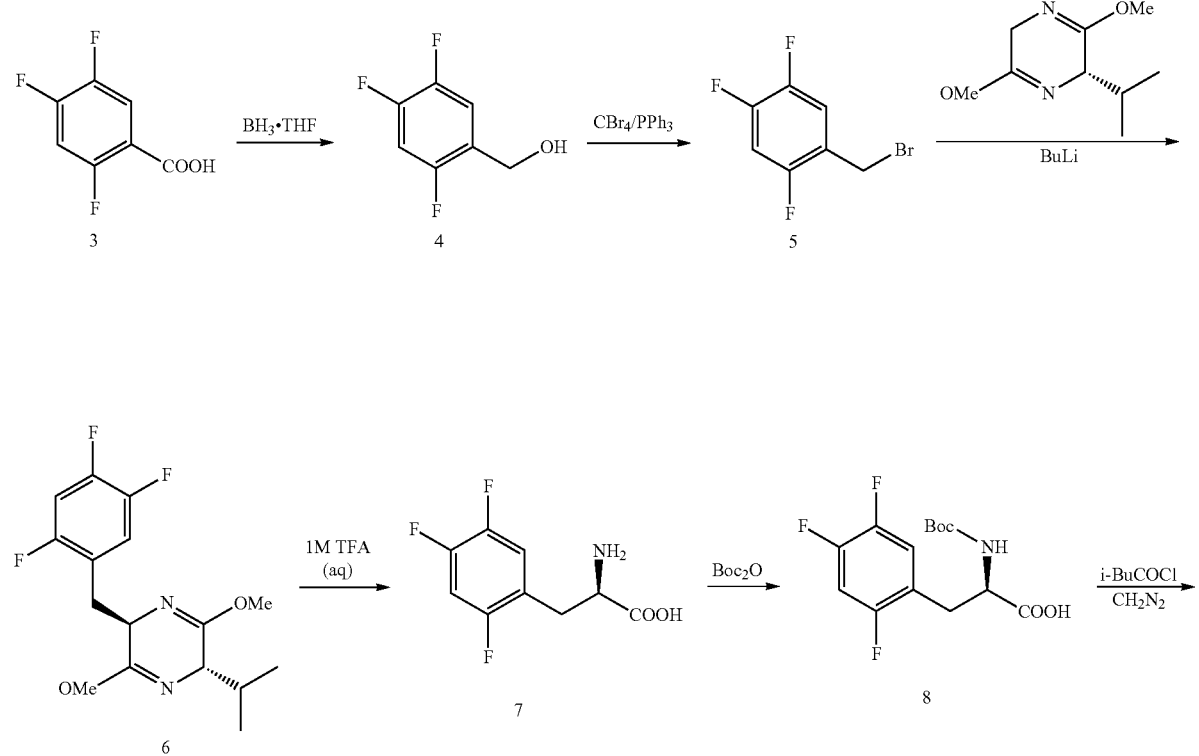

-continued

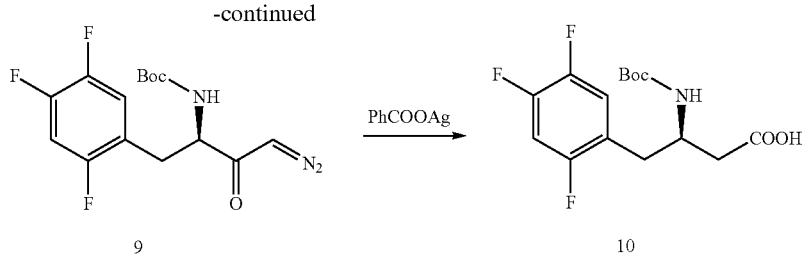

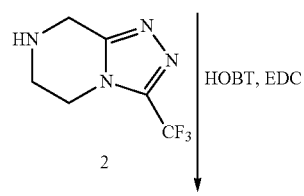

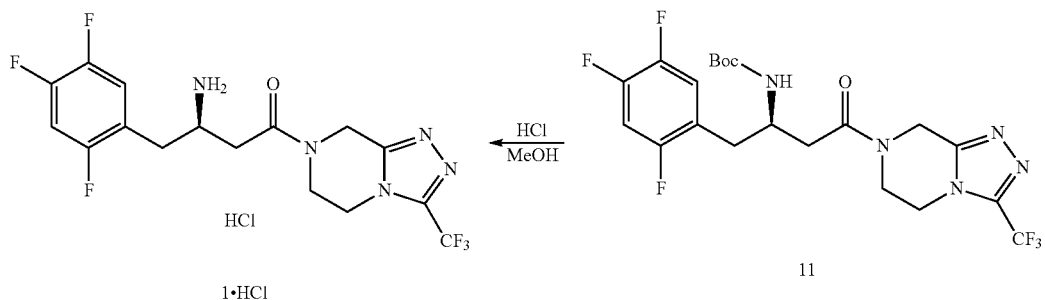

Since then, several trials to improve this unacceptable method have been published in literature. In general, regarding the structure of sitagliptin, which is composed from the β-amino acid part and the heterocyclic part, synthetic routes can be divided in two approaches.

In the first general approach, a heterocycle is coupled to the system in earlier steps of the synthesis, while the desired configuration of β-amino acid part is constructed later. This approach seems less feasible, because typically, it is better to couple more complicated and more expensive parts of molecule in last steps. A typical example of this approach is shown in Scheme 2.

Scheme 2

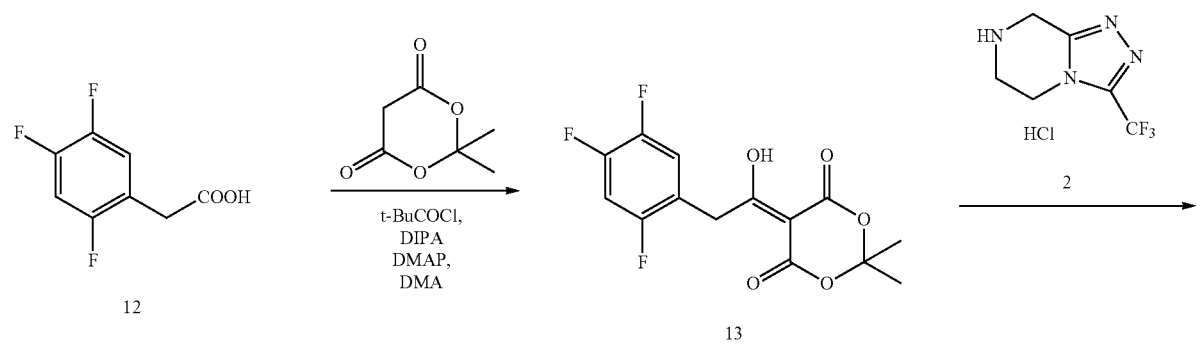

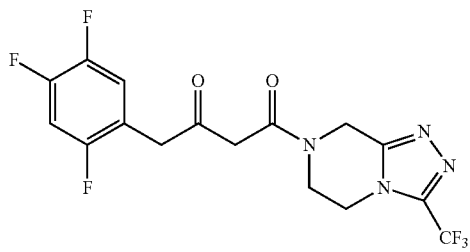

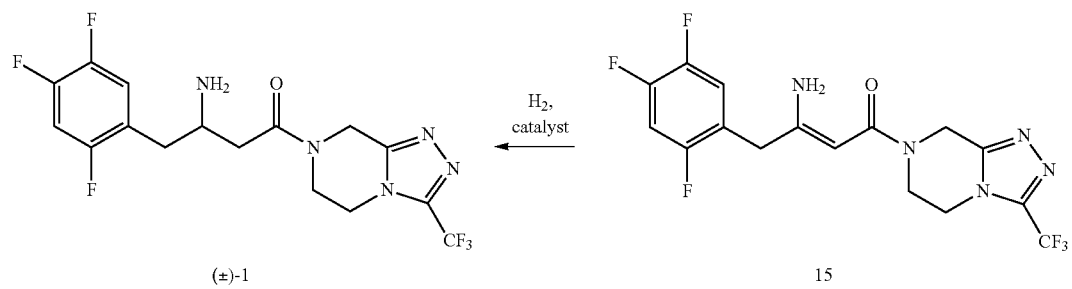

There is no good method for non-chromatographical chiral resolution of final compound 1 (WO 09/084024), so the resolution is performed by enantioselective reduction of 15 to 1. Such enantioselective hydrogenation of β-enamino acid derivatives requires expensive precious metal catalysts, such as rhodium (WO 03/004498, Tetrahedron Asymmetry 17, 205 (2006)) or ruthenium (WO 09/064476) and expensive ligands, such as ferrocenyl diphosphine ligands—JOSIPHOS catalysts (WO 04/085378, WO 05/097733, WO 06/081151, WO 11/113399, J. Am. Chem. Soc., 126, 9918 (2004)), while the compound 15 is less suitable for routine chiral enzymatic approaches due to bulky unnatural derivatisation of carboxylic part.

Another option is a derivatization of the amino group with a chiral group. Chiral resolution is then achieved by hydrogenation with a cheaper achiral catalyst, by crystallisation of diastereomeric mixtures or by combination of both methods, as depicted in Scheme 3 (WO 04/085661, WO 09/085990, WO 11/025932, WO 11/060213, WO 11/142825). These methods suffer from considerable loss of material in order to obtain pharmaceutical grade chiral purity.

Scheme 3

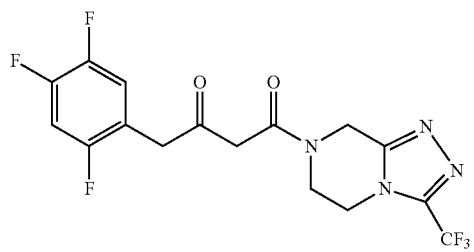

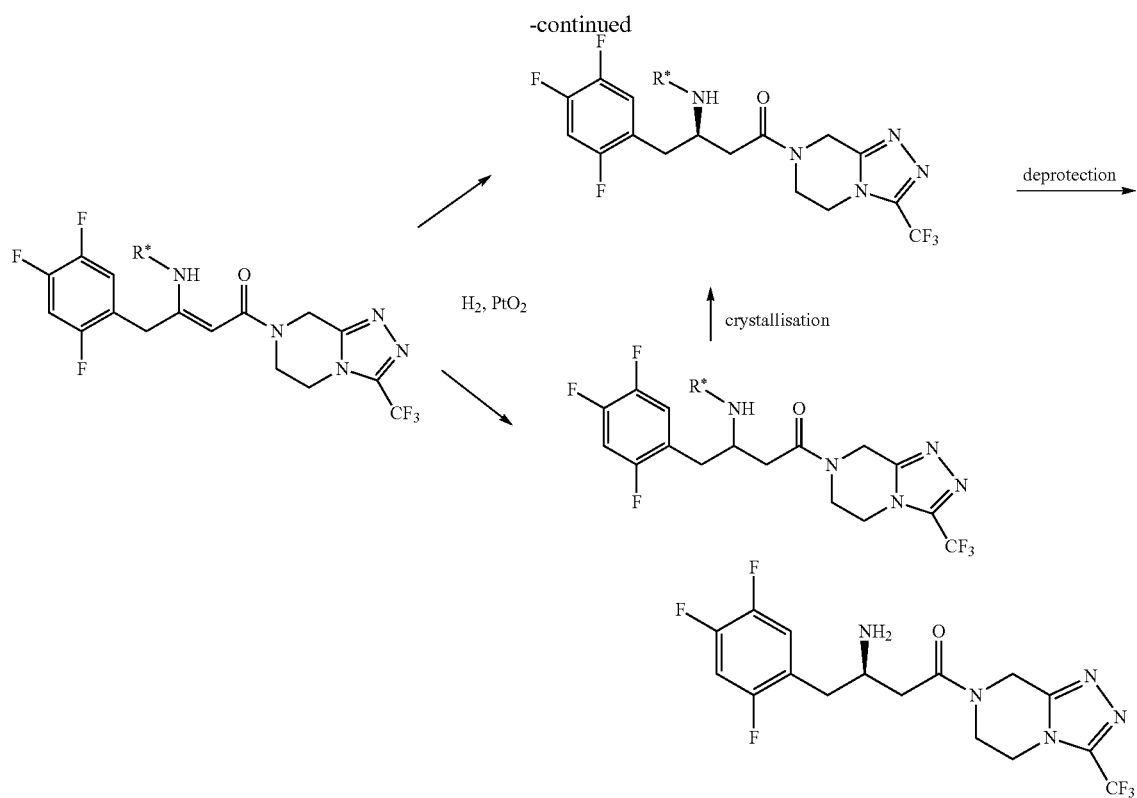

In the second general approach, a heterocycle is coupled to the β-amino acid in later steps. The corresponding δ-aryl-β-amino acids are readily available from the corresponding β-keto acids, prepared from acetic acids and malonic derivatives (WO 09/064476, WO 10/122578, WO 10/131025, WO 11/127794). Unfortunately, the amino group needs protection before coupling with the heterocycle in order to eliminate side reactions. As can be gathered from Scheme 4, the protection/deprotection scenario considerably prolongs the synthesis of antidiabetic agents (Scheme 4).

Scheme 4

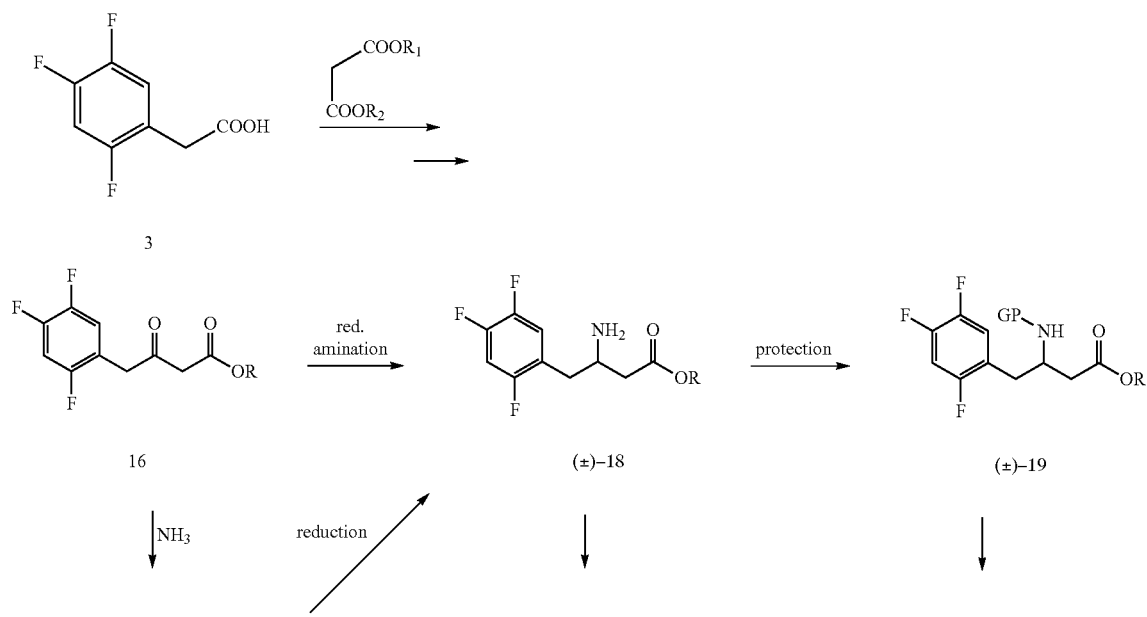

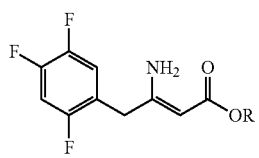
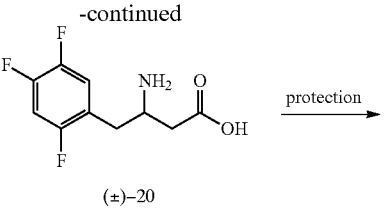
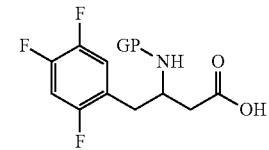

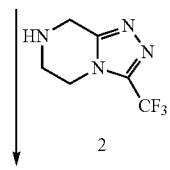

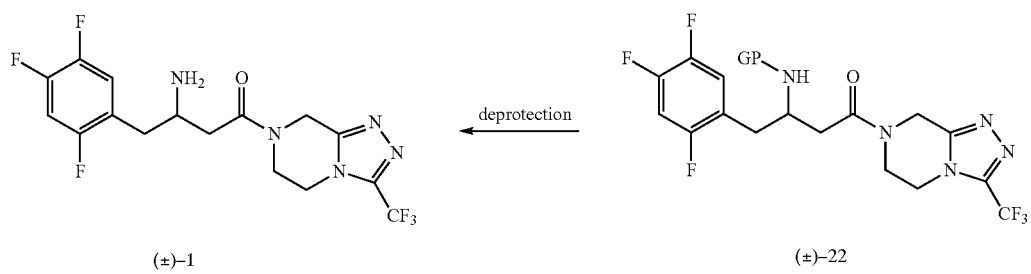

PG...protecting group

There are several methods in literature how to prepare enantiomerically enriched or pure intermediates 18, 19, 20, and 21, such as by enantioselective reduction of 17 (WO 09/064476), by introducing chiral protecting groups with further diastereoselective crystallization (CN 102126976), by crystallization of diastereomeric salt of compounds (±)-18, (±)-19, (±)-20, or (±)-21 with chiral acids (WO 10/122578, WO 10/131025, J. Chem. Res. 2010 (4), 230), or by introduction of a chiral center via natural source, such as aspartic acid derivatives (WO 11/035725, WO 11/116686A2, CN 102093245, CN 10212697) or by enzymatic approach.

Yet another option is creating a chiral center by selective reduction of β-keto acid derivatives. Precious metal catalysts (WO 04/087650, Org. Prep. Res. & Dev. 9, 634-639 (2005)) or enzymatic reduction (WO 09/045507) can be used, while the transformation of the obtained chiral hydroxyl intermediates to final sitagliptin precursors via azetidinone intermediates is laborious, as can be gathered from Scheme 5.

Scheme 5

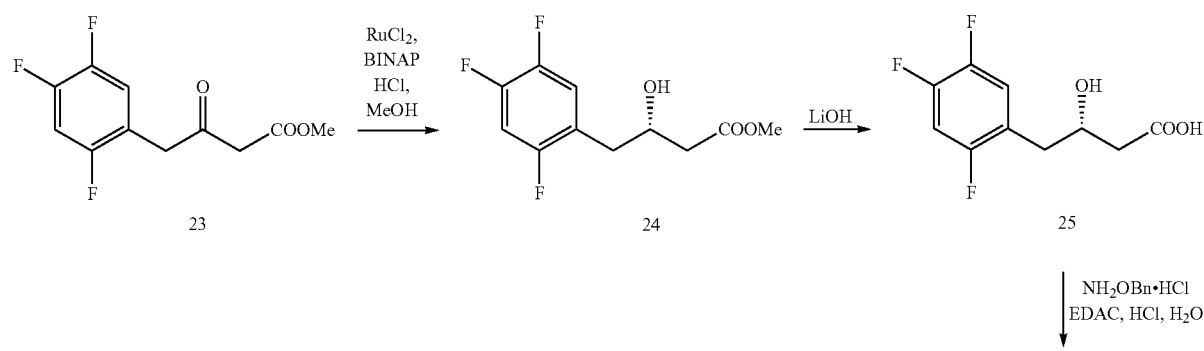

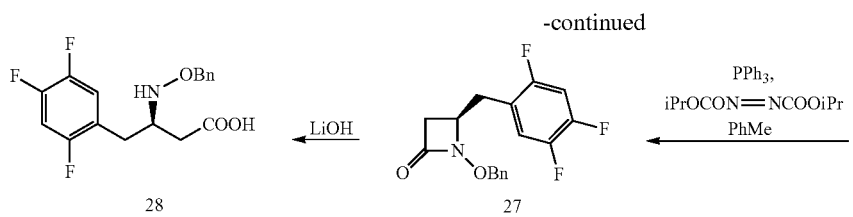
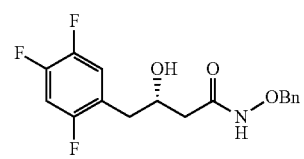
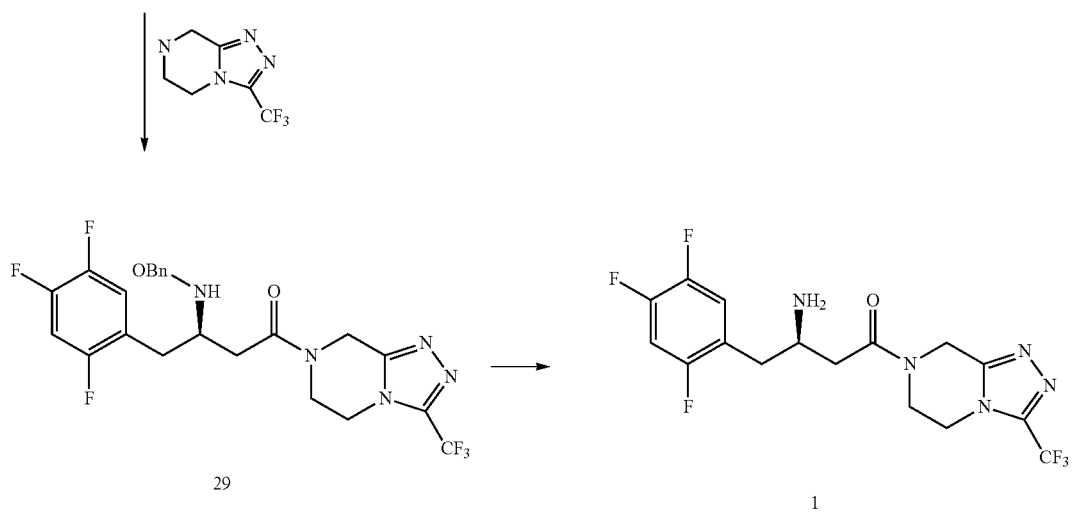

A hypothetical shortening of this conversion could be realized by preparation of an N-unsubstituted azetidinone having the structural formula

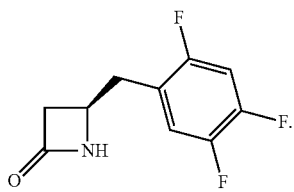 [SMILES: O=C1C[C@@H](Cc2cc(F)c(F)cc2F)N1]

However, the synthesis is very complicated and is realized by introduction of toxic hydroxylamine. In a characteristic literature example, only the non-fluoro analogue of the aforementioned N-unsubstituted azetidinone is prepared, while 2,4,5-fluoro analogues were prepared according to the reaction pathway depicted in Scheme 4, that is not via azetidinone derivatives (Org. Biomol. Chem., 8, 893 (2009)). Furthermore, an opening of the four-member ring of the N-unsubstituted azetidinone with nitrogen nucleophiles is accomplished by a complex reaction mixture with carbonic acid derivatives such as tert-butyl dicarbonate or chloroformates (WO 04/089362, WO 08/019124, Bioorg. Med. Chem. Lett. 13, 241 (2003, Tetrahedron Lett. 43, 3951 (2002), Org. Biomol. Chem, 1, 2670 (2003), ES 2335380).

Therefore, there is still a need for a simplification of industrial synthesis of β-amino acid derivatives as intermediates in the synthesis of dipeptidyl peptidase-4 (DPP-4) inhibitors such as sitagliptin.

OBJECT OF THE INVENTION

It was therefore an object of the present invention to provide an improved process for preparing β-aminobutyryl substituted 5,6,7,8-tetrahydro[1,4]diazolo[4,3-α]pyrazin-7-yl compounds representing valuable key intermediates for the preparation of pharmaceutically active agents or representing a pharmaceutically active agent such as dipeptidyl peptidase-4 (DPP-4) inhibitors, e.g. sitagliptin.

SUMMARY OF THE INVENTION

Various aspects, advantageous features and preferred embodiments of the present invention as summarized in the following items, respectively alone or in combination, contribute to solving the object of the invention.

(1) A process for the preparation of a compound of formula IV,

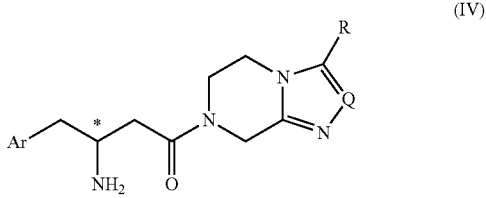

wherein Ar denotes unsubstituted or substituted C6-C12-aryl, Q denotes N, CH or a carbon substituted with unsubstituted or substituted C1-C6-alkyl, C6-C12-aryl or C7-C12-alkylaryl, and R denotes H or unsubstituted or substituted C1-C6-alkyl, C6-C12-aryl or C7-C12-alkylaryl, comprising a step of coupling a compound of formula II,

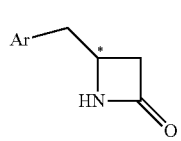

(II)

wherein Ar is defined as above,
with a compound of formula III or a salt thereof,

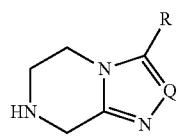

(III)

wherein R and Q are defined as above,
in the presence of a catalyst in an organic solvent.

The designation "*" in the structural formulae of compounds of formula IV and III indicates a chiral center.

The term "chiral center" as used herein means a tetrahedral carbon atom having four different substituents attached thereto. The arrangement of these different substituents around the asymmetric atom determines its optical activity which is denoted in the art by the terms S or R and D or L respectively.

The term "alkyl" as used herein means straight, branched or cyclic hydrocarbons.

The term "aryl" as used herein means hydrocarbon aryls, preferably single or condensed six-membered rings, more preferably phenyl or naphthyl, in particular phenyl.

The term "alkylaryl" as used herein means that the aforementioned aryl moieties are incorporated into the aforementioned straight or branched alkyl moieties either at one of the proximal or distal ends of the alkyl chain or between the aforementioned alkyl chains. For example, for substituent Q, proximal end means adjacent to the carbon of Q incorporated into the di- or triazole ring of the heterocyclic moiety of compound of formulae III and IV, while distal means the terminal carbon of the alkyl moiety which is furthermost from substituent Q. Preferably, in the alkylaryl moiety, the aryl moiety is located at the distal end of the alkyl moiety.

The term "substituted" as employed herein in connection with Ar, Q and R means that the alkyl, aryl and alkylaryl groups have at least one $C_1$-$C_6$ alkyl, $C_1$-$C_6$ alkoxy and/or at least one halogen substituent selected from the group consisting of F, Cl, Br and I.

The term "catalyst" as employed herein represents a substance, which enables or accelerates a reaction, while not becoming a covalent part of any product of the final reaction mixture. The catalyst can be used in submolar, molar, or excessive amounts.

(2) The process according to item (1), wherein the chiral center of the compound of formula IV and the compound of formula II is in R-configuration, respectively.

The designations "R" and "S" used herein indicate the absolute configuration at chiral center(s) of the respective compounds, determined by means of the Cahn Ingold Prelog convention (CIP-convention) known in the art (cf. e.g. M. B. Smith, J. March, "March's Advanced Organic Chemistry: Reactions, Mechanisms and Structure", 6$^{th}$ edition, John Wiley&Sons, Inc., p. 155-158).

Compound of formula IV in R-configuration has the following structural formula,

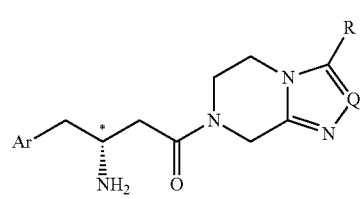

(IV)

wherein the dashed C—N bond indicates that this bond is located below the plane of the paper according to the CIP-convention.

(3) The process according to item (1) or (2), wherein in the compounds of formulae II and IV, Ar is substituted phenyl, preferably fluorine substituted phenyl, in particular 2,4,5-trifluoro-phenyl.

(4) The process according to any one of the preceding items, wherein in the compounds of formulae II and IV, R is substituted C1-C3-alkyl, preferably halogen substituted C1-C3-alkyl, more preferably fluoro substituted C1-C3-alkyl, in particular trifluoromethyl.

(5) The process according to any one of the preceding items, wherein in the compounds of formulae II and IV, Q is N.

(6) The process according to any one of the preceding items, wherein Ar is 2,4,5-trifluorophenyl, R is trifluoromethyl, Q is N and the chiral center is in R-configuration.

(7) The process according to any one of the preceding items, wherein the compound of formula III is provided in the form of its acid addition salt, preferably in the form of its hydrochloride salt.

(8) The process according to any one of the preceding items, wherein the solvent is selected from the group of C2-C8 aliphatic ethers, C4-C6 cyclic ethers, C1-C4-alkyl C1-C4-alkanoates, aliphatic nitriles, C1-C2-alkanamides, dimethylsulfoxide, and C1-C4-alcohols, preferably the solvent is selected from symmetric di-(C2-C4-alkyl) ethers or asymmetric di-(C1-C4-alkyl) ethers, tetrahydrofuran, methanol, toluene, hexane or isopropyl acetate, in particular the solvent is acetonitrile or tetrahydrofuran.

(9) The process according to any one of the preceding items, wherein the catalyst is selected from Broensted or Lewis acids.

(10) The process according to the item (9), wherein the Broensted acid is selected from water, inorganic acids, preferably selected from HCl, HBr, sulphuric acid, phosphoric acid, boric acid, or organic acids, preferably selected from C1-C12-alkanecarboxylic acid, most preferably acetic acid, or C7-C9-alkanecarboxylic acid, in particular 2-ethylhexanoic acid (2-EHA), or unsubstituted or fluoro substituted C1-C4-alkanesulfonic acids, most preferably trifluoromethanesulfonic acid or arenesulfonic acid, most preferably p-toluenesulfonic acid.

(11) The process according to the item (10), wherein the Broensted acid is applied in a form of an addition salt with the compound of formula III, preferably as a hydrochloride salt, wherein HCl is used as a catalyst.

(12) The process according to the items (10) and (11), wherein the Broensted acid is used in at least equimolar amount.

(13) The process according to the item (9), wherein the Lewis acid is selected from iron, zinc, or copper salts, preferably from copper (II) chloride.

(14) The process according to any one of the preceding items, wherein the compound of formula II,

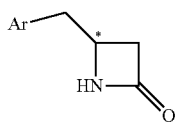

(II)

wherein Ar denotes unsubstituted or substituted aryl,
is provided in substantially enantiopure form; preferably substantially enantiopure compound of formula II' or II" having the structural formula

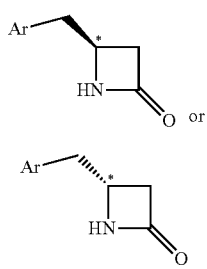

(II')

or (II")

wherein Ar is defined as above,
is prepared by subjecting racemic or enantioenriched compound of formula II,

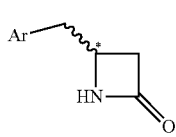

(II)

wherein Ar is defined as above,
to kinetic resolution by means of a hydrolytic enzyme in the presence of an organic solvent, wherein one kind of enantiomer of the compound of formula II is converted to a compound of formula I,

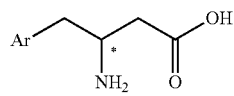

(I)

wherein Ar is defined as above,
while the other enantiomer of the compound of formula II remains substantially unreacted.

The term "substantially enantiopure" as used herein means that a compound has an enantiomeric excess of at least 80%, preferably at least 90%, more preferably at least 95%, even more preferably at least 98%.

The term "hydrolytic enzyme" as used herein means an enzyme which is capable to hydrolyze a covalent bond. In particular, in the present process, an amide bond is hydrolyzed, whereby the lactame ring of compound of formula II is opened.

The term "enantiomer" as used herein means two stereoisomers which are mirror images of one another, but which are not superimposable. In the case of compound of formulae II and IV, in case the chiral center "*" is in the form of the R-configuration according to the CIP-convention, compounds of formula II and III represent R-enantiomers. On the other hand, in case the chiral center "*" is in the form of the S-configuration according to the CIP-convention, compounds of formula II and III represent S-enantiomers.

The term "enantiopure" as used herein means that an enantiomer is present in a purity of at least 99% enantiomeric excess, preferably in a purity of 99.5-100% enantiomeric excess.

The term "substantially unreacted" as used herein means that at least 80% of the other enantiomer of compound of formula II remains unreacted, preferably at least 90%, more preferably at least 95%, even more preferably at least 98%, in particular 100% of the other enantiomer remains unreacted.

(15) The process according to item (14), wherein the S-enantiomer of compound of formula II is converted to compound of formula I, while the R-enantiomer of compound of formula II remains substantially unreacted.

(16) A process for preparing a substantially enantiopure compound of formula IIa"

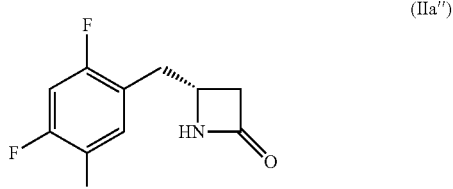

(IIa")

wherein chiral center is in R-configuration,
in which process a racemic or enantioenriched compound of formula IIa

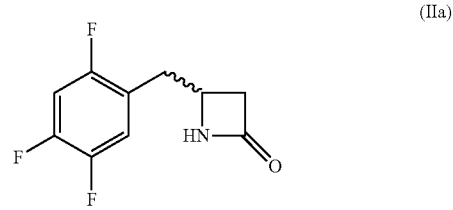 [SMILES: O=C1CC(Cc2cc(F)c(F)cc2F)N1]

(IIa)

is subjected to kinetic resolution by means of a hydrolytic enzyme in the presence of an organic solvent, wherein the S-enantiomer of compound of formula IIa" is converted to a compound of formula Ia',

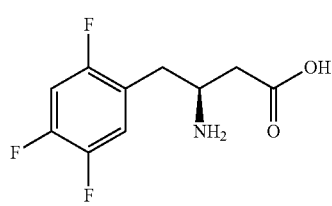

(Ia')

while the R-enantiomer of compound of formula IIa' remains substantially unreacted.

As regards the meanings of the terms "substantially enantiopure", "hydrolytic enzyme", "enantiomer", "enantiopure", and "substantially unreacted" reference is made to the explanations under item (14) above.

(17) The process according to any one of items (14) to (16), wherein compound of formula II provided as the starting material is in racemic form.

(18) The process according to any one of items (14) to (17), wherein the hydrolytic enzyme is selected from the class of lipases, esterases, aminoacylases, amidases, peptidases and amylases.

(19) The process according to item (18), wherein the hydrolytic enzyme is selected from the group of lipases, preferably from *Candida antarctica* lipase A and *Candida antarctica* lipase B, most preferably *Candida antarctica* lipase B.

(20) The process according to any one of items (14) to (19), wherein the process is carried out at the temperature from 25° C. to 70° C., preferably from 30° C. to 60° C., in particular from 40° C. to 55° C.

(21) The process according to any one of items (14) to (18), wherein the enzyme is immobilised on a polymer resin, preferably on a polyacrylic resin.

(22) The process according to any one of items (14) to (21), wherein the load of immobilized enzyme is from 10 g/L to 500 g/L, preferably from 20 g/L to 300 g/L, in particular from 25 g/L to 250 g/L.

(13) The process according to any one of items (14) to (22), wherein the ratio of immobilized enzyme to substrate is from 1:1 to 20:1.

(24) The process according to any one of items (14) to (19), wherein the compound of formula II" or IIa" obtained after enzymatic racemic resolution has an enantiomeric excess (ee) of at least 80%, preferably at least 90%, more preferably at least 95% and in particular at least 98%.

The term "enantiomeric excess" as used herein means the difference between the percentage of one enantiomer of an optically active compound and the percentage of the other enantiomer of the same optically active compound. For example, an optically active compound which contains 75% R-enantiomer and 25% S-enantiomer will have an enantiomeric excess of 50% of R-enantiomer.

As regards the definition of the term "enantiomer", reference is made to the explanations under item (14) above.

(25) The process according to any one of items (14) to (24), wherein the organic solvent is selected from C5-C7 alkanes, C2-C8 aliphatic ethers, C4-C6 cyclic ethers, C1-C4-alkyl C1-C4-carboxylates and C1-C4-alcohols and toluene, preferably the solvent is selected from symmetric di-(C2-C4-alkyl) ethers or asymmetric di-(C1-C4-alkyl) ethers, in particular diisopropyl ether (i-Pr$_2$O) or methyl tert-butyl ether.

(26) The process according to any one of items (14) to (25), wherein subsequent to removal of the hydrolytic enzyme, compound of formula I or compound of formula Ia is separated from the resulting reaction mixture by means of separation, preferably by separation selected from the group consisting of filtration, centrifugation or decantation, more preferably filtration.

(27) A process for preparing compound of formula I

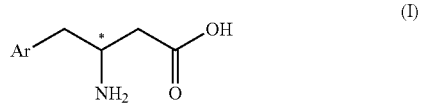

(I)

in racemic form, the process comprising the steps of:
i) oxidation of a compound of formula I in enantioenriched or enantiopure form to its C—N double bonded intermediates by means of an oxidizing agent, and
ii) reduction of the C—N double bonded intermediates obtained in step i) by means of a reducing agent,
in order to obtain compound of formula I in racemic form.

The term "racemisation" as used herein means that a compound in enantioenriched or (substantially) enantiopure form is converted to its racemic form, that is a 1:1 mixture of the respective enantiomers.

The term "enantioenriched" means, that a compound has an enantiomeric excess higher than zero.

As regards the meaning of the term "enantiopure", reference is made to the explanations under item (14) above.

Preferably, both step i) and ii) of the racemisation process are carried out in a one-pot process. That is, steps i) and ii) are carried out in the same reaction vessel.

(28) The process according to item (27), wherein compound of formula I is provided in (substantially) enantiopure form, preferably (substantially) enantiopure compound of formula I'

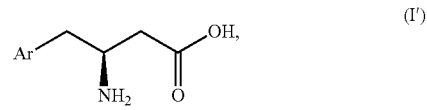

(I')

which chiral center is in S-configuration is provided.

As regards the meaning of the term "(substantially) enantiopure", reference is made to the explanations under item (14) above.

(29) The process according to item (27) or (28), wherein in step i) and ii), pH of the reaction mixtures is suitably adjusted in view of the oxidizing and reducing agent respectively applied.

(30) The process according to any one of items (27) to (29), wherein subsequent to step i) and prior to step ii), water and/or organic solvents are removed from the reaction mixture.

(31) The process according to any one of items (27) to (30), wherein the oxidizing agent is potassium peroxymonosulfate (KHSO$_5$) and/or the reducing agent is elemental zinc (Zn).

(32) The process according to item (31), wherein the oxidizing agent is potassium peroxymonosulfate (KHSO$_5$) and pH is adjusted to from 7 to 10, preferably from 7 to 9, in particular to 9.

(33) The process according to item (31), wherein the reducing agent is elemental zinc (Zn) and pH is adjusted to pH lower than 4, preferably lower than 2 using mineral acids, preferably hydrochloric acid or acetic acid.

(34) The process according to any one of items (28) to (34), wherein compound of formula I is prepared via a process according to any one of items (14) to (26).

(35) The process according to any one of items (14) to (26), wherein at least a part of the amount of compound of formula II is prepared according to the process of any one of items (27) to (34).

(36) The process according to any one of the preceding items, wherein the compound of formula II

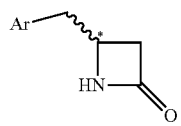

is prepared from a compound of formula I

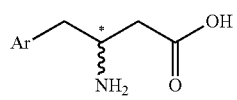

by means of a cyclodehydration reaction.

The term "cyclodehydration reaction" as used herein means a reaction in which a ring is formed by means of dehydration, that is by removal of water.

Preferably, in the cyclodehydration reaction, compound of formula I is provided in form of (substantially) enantiopure compound of formula I″

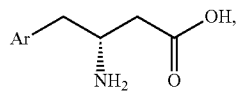

wherein chiral center is in R-configuration.

As regards the meaning of the term "(substantially) enantiopure", reference is made to the explanations under item (14) above.

(37) The process according to item (36), wherein cyclodehydration is carried out by applying an C1-C6-alkanesulfonyl chloride or arylsulfonyl chloride and a proton acceptor as reactants, preferably methanesulfonyl chloride (MeSO₂Cl) and NaHCO₃ are applied as reactants.

The term "proton acceptor" as used herein means a Brønsted base which provides for accepting protons of acids.

(38) The process according to item (36) or (37), wherein compound of formula I is prepared according to a process according to any one of items (14) to (26).

(39) The process according to any one of items (1) to (15), wherein compound of formula II is prepared according to the process of any one of items (36) to (38).

(40) The process according to any one of items (1) to (15), for a preparation of a compound of formula IV in (R) configuration, wherein the compound of formula II is prepared by the following steps:
  1) providing an S-enantiomer of compound of formula I,
  2) racemizing the compound of step 1) according to any one of items 27 to 34,
  3) submitting the compound of step 2) to the cyclodehydration reaction of item 36 or 37 to form the compound of formula II.

(41) A process for the preparation of a pharmaceutical composition comprising compound of formula IV or a pharmaceutically acceptable salt thereof as pharmaceutically active ingredient, comprising the steps of:
  a) preparing a compound of formula IV or a salt thereof according to the process according to any one of items (1) to (15), (18) to (26), (34) and (40), and
  b) admixing the prepared compound of formula IV or pharmaceutically acceptable salt thereof with at least one pharmaceutically acceptable excipient.

(42) The process according to item (41), wherein the compound of formula IV is sitagliptin having the structural formula,

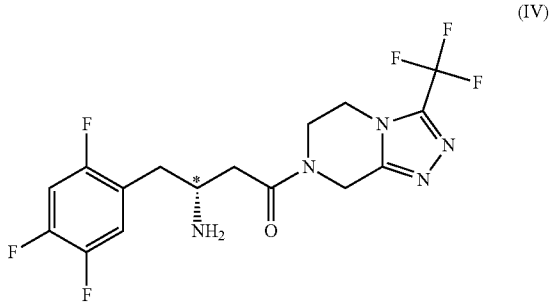 [SMILES: N[C@@H](CC(=O)N1CCn2c(nnc2C(F)(F)F)C1)Cc1cc(F)c(F)cc1F]

preferably sitagliptin is in the form of its phosphate salt.

(43) The pharmaceutical composition according to item (41) or (42), which composition comprises at least one additional pharmaceutically active ingredient besides of compound of formula IV, wherein said additional pharmaceutically active ingredient is selected from the group consisting of insulin sensitizers, insulin, insulin mimetics, sulfonylureas, α-glucosidase inhibitors, glucagon receptor antagonists, GLP-1, GLP-1 analogues, GLP-1 mimetics, GLP-1 receptor agonists, GIP, GIP mimetics, PACAP, PACAP mimetics, PACAP receptor agonists, cholesterol lowering agents, PPARδ-agonists, anti-obesity compounds, ileal bile acid transporter inhibitors, agents intended for use in inflammatory conditions, antihypertensive agents, glucokinase activators (GKAs), inhibitors of 11(-hydroxysteroid dehydrogenase type 1, inhibitors of cholesteryl ester transfer protein (CETP) and inhibitors of fructose 1,6-bisphosphatase.

(44) The pharmaceutical composition according to item (42), wherein the additional pharmaceutically active ingredient is metformin and/or its pharmaceutically acceptable salt.

DETAILED DESCRIPTION OF THE INVENTION

The present invention will now be described in further detail with respect to preferred embodiments and specific examples, which embodiments and examples are however presented for illustrative purposes only and shall not be understood as limiting the scope of the present invention.

Compared with the conventional synthetic pathways for preparing a compound of formula IV requiring a large number of synthetic steps and typically protection and deprotection of the amine group of an intermediate β-aminoacid derivative, the present invention surprisingly satisfies an unmet need for a significant improvement of a process for preparing a compound of formula IV that is suitable for industrial production of an pharmaceutically active agent such as dipeptidyl peptidase-4 (DPP-4) inhibitors, for example sitagliptin.

In particular, the present invention provides an industrially applicable, economical and advantageous process for the preparation of a compound of formula IV,

wherein Ar denotes unsubstituted or substituted C6-C12-aryl, Q denotes N, CH or a carbon substituted with unsubstituted or substituted C1-C6-alkyl, C6-C12-aryl or C7-C12-alkylaryl, and R denotes H or unsubstituted or substituted C1-C6-alkyl, C6-C12-aryl or C7-C12-alkylaryl, which process comprises a step of coupling a compound of formula II,

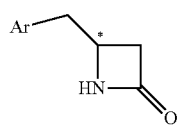

wherein Ar is defined as above,
with a compound of formula III or salt thereof,

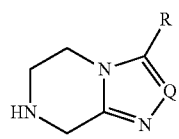

wherein R and Q are defined as above,
in the presence of a catalyst in an organic solvent.

The above procedural concept provides for a particularly efficient preparation of compounds of formula IV. In particular, it was surprisingly found that a heterocyclic compound of formula III can be readily substituted with a β-amino acid by means of a single coupling step, wherein compound of formula IV is obtained in both high yields and purity, while it can be dispensed with e.g. conventional application of a protecting group for the amine moiety of the β-amino acid. Owing to the finding that protecting group application technology can be dispensed with, the preparation of a compound of formula IV can be reduced by at least two process steps, namely introduction and removal of a protecting group and both isolation and purification of the respective intermediate products obtained in said steps. Furthermore, the starting materials compound of formula II and III are readily available by established prior art synthesis.

According to a preferred embodiment of the invention, compound(s) of formula II, III and/or IV is/are characterized by either one or a combination of the following features i) to vi):

i) the chiral center of compound of formula II and IV is in R-configuration;
ii) in compounds of formulae II and IV, Ar is substituted phenyl, preferably fluorine substituted phenyl, in particular 2,4,5-trifluorophenyl;
iii) in compounds of formulae II and IV, R is substituted C1-C3-alkyl, preferably halogen substituted C1-C3-alkyl, more preferably fluoro substituted C1-C3-alkyl, in particular trifluoromethyl;
iv) in compounds of formulae II and IV, Q is N;
v) Ar is 2,4,5-trifluorophenyl, R is trifluoromethyl, Q is N and the chiral center is in R-configuration.
vi) compound of formula III is provided in the form of its pharmaceutically acceptable acid addition salt, preferably in the form of its hydrochloride salt,

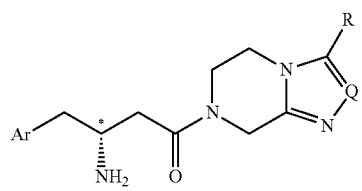

wherein the dashed C—N bond indicates that this bond is located below the plane of the paper according to the CIP-convention.

In the aforementioned preferred embodiment, the configuration at the chiral center and substituents Ar, R and Q of compounds of formula IV, III and II are respectively suitably selected from features i) to vi) in order to provide for a particularly smooth coupling reaction and in order to obtain compounds of formula IV which represent particularly desirable pharmaceutically active agents and/or intermediate products for preparing pharmaceutically active agents. In particular, selection of feature vi) provides for the pharmaceutically active agent sitagliptin having the structural formula

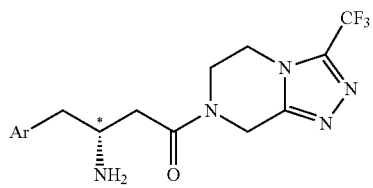

as coupling product.

In another preferred embodiment, the coupling process is characterized by either one or a combination of the following procedural features:

the solvent is selected from the group of C2-C8 aliphatic ethers, C4-C6 cyclic ethers, C1-C4-alkyl C1-C4-alkanoates, aliphatic nitriles, C1-C2-alkanamides, dimethylsulfoxide, and C1-C4-alcohols, preferably the solvent is selected from symmetric di-(C2-C4-alkyl) ethers or asymmetric di-(C1-C4-alkyl) ethers, tetrahydrofuran, methanol, toluene, hexane or isopropyl acetate, in particular the solvent is acetonitrile or tetrahydrofuran; and/or the catalyst is selected from Broensted or Lewis acids, wherein the Broensted acid is selected from inorganic acids, preferably selected from water, or mineral acids, such as HCl, HBr, sulphuric acid, phosphoric acid, boric acid, or organic acids selected from C1-C12-alkanecarboxylic acid, most preferably acetic acid, or C7-C9-alkanecarboxylic acid, in particular 2-ethylhexanoic acid (2-EHA), and/or unsubstituted or fluoro substituted C1-C4-alkanesulfonic acids, most preferably trifluoromethanesulfonic acid or arenesulfonic acid, most preferably p-toluenesulfonic acid, and wherein the Lewis acid is selected from iron, zinc, or copper salts, such as $ZnCl_2$, $FeCl_2$, and $CuCl_2$.

Thereby, solvent and catalyst are suitably selected in order to provide for particularly advantageous conversion rate to compound of formula IV. In a preferred case the acid catalyst is used in at least equimolar amount. In one special, but not a limited case, Broensted and Lewis acid could be combined.

According to yet another preferred embodiment of the invention, compound of formula III is provided in the form of its acid addition salt, preferably in the form of its hydrochloride salt. It is surprisingly found that the acid addition salt may have a role of an acidic catalyst, if it is used in at least equimolar amount and no additional acid is needed. This is contrary to the prior art method wherein 2-ethylhexanoic acid is used to accomplish reaction. If the acid is used in submolar amount or the compound of formula II in neutral form is used the starting material is submitted only to limited conversion.

Alternatively, compound of formula III is provided as a free base.

Preferably, compound of formula II,

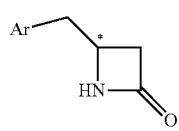

wherein Ar denotes unsubstituted or substituted aryl,
is provided in substantially enantiopure form.

According a particularly preferred embodiment, substantially enantiopure compound of formula II' or II" having the structural formula

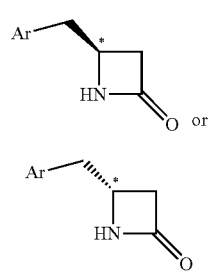

wherein Ar is defined as above,
is prepared by subjecting racemic or enantioenriched compound of formula II,

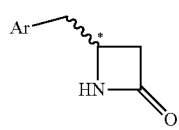

wherein Ar is defined as above,
to kinetic resolution by means of a hydrolytic enzyme in the presence of an organic solvent, wherein one kind of enantiomer of compound of formula II is converted to a compound of formula I,

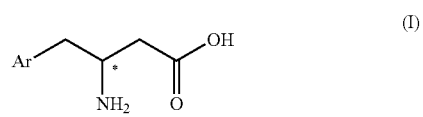

wherein Ar is defined as above,
while the other enantiomer of compound of formula II remains substantially unreacted.

In this way, (substantially) enantiopure compound of formula II" is obtained by means of enzymatic kinetic resolution. In particular, it was surprisingly found that by means of enzymatic kinetic resolution, one enantiomer of compound of formula II can be converted to compound of formula I, while the other enantiomer of compound of formula II remains substantially unreacted.

In particular, in this kinetic resolution an individual one, e.g. the "undesired" enantiomer of compound of formula II, is converted to compound of formula I which can be easily separated by physical and/or chemical methods from compound of formula II, while the other individual one, e.g. the "desired" enantiomer of compound of formula II is converted in a lesser extend, preferably compound of formula II is not or at least substantially not converted to compound of formula I. By providing compound of formula II in substantially enantiopure form in the coupling process for preparing compound of formula IV, it can be dispensed with subsequent laborious and costly racemic resolution of compound of formula IV, e.g. by means of conventional formation of diastereomeric salts.

Preferably, the S-enantiomer of compound of formula II is converted to compound of formula I, while the R-enantiomer of compound of formula II remains substantially unreacted.

According to another aspect of the present invention, a process for preparing substantially enantiopure compound of formula IIa"

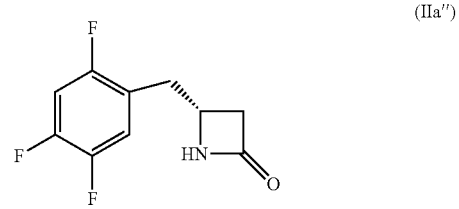 [SMILES: O=C1C[C@@H](Cc2cc(F)c(F)cc2F)N1]

which chiral center is in R-configuration,
is provided, in which process a racemic or enantioenriched compound of formula IIa

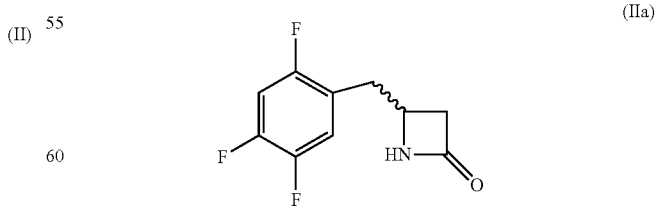

is subjected to kinetic resolution by means of a hydrolytic enzyme in the presence of an organic solvent, wherein the S-enantiomer of compound of formula IIa' is converted to a compound of formula Ia'

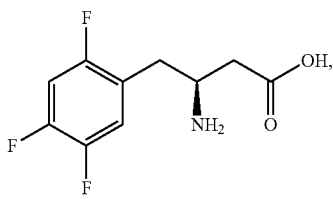

while the R-enantiomer of compound of formula IIa" remains substantially unreacted.

According to this further aspect of the invention, compound of formula IIa" can be provided in (substantially) enantiopure form by means of enzymatic kinetic resolution. It was surprisingly found that compound of formula IIa representing a valuable intermediate for preparing a pharmaceutically active compound such as sitagliptin is a particularly suitable substrate for enzymatic kinetic resolution. It is well known in the art that enzyme activity and also its stereochemical outcome depend on the electronic and steric nature of substituents in the substrate. Although compound IIa contains three fluorine atoms on the aromatic ring that result in bulkier and very electron deficient aromatic system it was surprisingly found that a successful enzymatic kinetic resolution by CaIB was achieved, which provided the substantially enantiopure form of compound IIa".

According to a preferred embodiment, in the above described processes for preparing compounds of formula II" and IIa" respectively by means of enzymatic kinetic resolution, compound of formula II provided as the starting material is in racemic form. The racemic form serves as a particularly suitable substrate for efficiently enantiomerically enriching compound of formula II by means of enzymatic kinetic resolution.

According to another preferred embodiment, the hydrolytic enzyme is selected from the group of lipases, preferably from *Candida antarctica* lipase A and *Candida antarctica* lipase B, most preferably *Candida antarctica* lipase B. In this way, hydrolytic enzymes are selected which are particularly suitable in view of the substrate in the form of compound of formula II, that is, enzymes having a particularly advantageous substrate specificity towards compounds of formula II.

Preferably, the enzyme is immobilised on a polymer resin, preferably on a polyacrylic resin. This provides for a simplified removal of the enzyme from the reaction mixture subsequent to termination of kinetic resolution reaction.

According to a preferred embodiment of the invention, compound of formula II" or IIa" obtained after enzymatic racemic resolution has an enantiomeric excess (ee) of at least 80%, preferably at least 90%, more preferably at least 95%, and in particular at least 98%.

Preferably, the organic solvent is selected from C5-C7 alkanes, C2-C8 aliphatic ethers, C4-C6 cyclic ethers, C1-C4-alkyl C1-C4-alkanoates and C1-C4-alcohols and toluene, preferably the solvent is selected from symmetric di-(C2-C4-alkyl) ethers or asymmetric di-(C1-C4-alkyl) ethers, in particular diisopropyl ether (i-Pr$_2$O) or methyl tert-butyl ether. Thereby, the solvent is suitably selected in order to provide for both compatibility with the enzyme and for particularly advantageous conversion rate to compound of formula II' or IIa'.

In a preferred embodiment, subsequent to removal of the hydrolytic enzyme, compound of formula I is separated from the resulting reaction mixture by means of separation, preferably by separation selected from the group consisting of filtration, centrifugation or decantation, more preferably filtration. In this way, separation of compound of formula I can be accomplished by simple means.

According to another aspect of the invention, a process for preparing compound of formula I

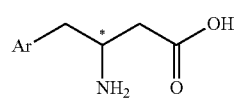

in racemic form is provided, the process comprising the steps of:
i) oxidation of a compound of formula I in enantioenriched or enantiopure form to its C—N double bonded intermediates by means of an oxidizing agent, and
ii) reduction of the C—N double bonded intermediates obtained in step i) by means of a reducing agent,
in order to obtain compound of formula I in racemic form.

According to this aspect of the invention, a particularly advantageous recycling concept is provided. In particular, enantioenriched or (substantially) enantiopure compound of formula I can be converted to its racemate, that is, up to 50% of an "undesired" enantiomer can be converted to the desired enantiomer. For example, in case the R-enantiomer of compound of formula I" is desired for a specific application, S-enantiomer of compound of formula I' can be readily converted to a racemate I comprising, 50% S-enantiomer and 50% R-enantiomer. The desired R-enantiomer can be provided as starting material in a preparation process, preferably a process according to item (1), while the undesired S-enantiomer can be again subjected to the racemisation process according to item (20).

Preferably, both steps i) and ii) of the racemisation process are carried out in a one-pot process. That is, steps i) and ii) are carried out in the same reaction vessel. In a preferred embodiment the same solvents are used in both steps. Alternatively, solvents used in the oxidation step are easily removed and replaced by the solvent suitable for the reduction step. Preferably, oxidizing and reducing agents are specially selected to act in media, which allow one-pot procedure.

According to a preferred embodiment of the invention, compound of formula I is provided in (substantially) enantiopure form, preferably (substantially) enantiopure compound of formula I',

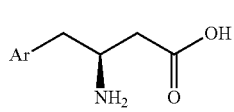

wherein chiral center is in S-configuration is provided. The (substantially) enantiopure form serves as a particularly suitable substrate for efficiently racemizing compound of formula I.

According to another preferred embodiment of the invention, oxidation agents are selected to efficiently racemize primary amines via C—N double bonded intermediates. Preferably, oximes as a tautomeric form of nitroso intermediates are the sufficiently stable C—N double bonded representatives, used for such conversion.

Preferably, oxidation agents are selected from tungsten (VI) compounds, preferably $Na_2WO_4$ or $WO_3$ in molar amounts or catalytic amounts with co-oxidant such as hydrogen peroxide, various peroxo compounds, formed in situ from hydrogen peroxide and a compound which is transformed to an active peroxo intermediate and is selected tungsten, vanadium, molybdenum compounds or used as isolated reagents such as dioxiranes, such as dimethyldioxirane, perbenzoic acids and salts, peroxysulfuric acid and salts. The most preferred reagents are sodium (VI) tungstate, dimethyldioxirane and potassium peroxymonosulfate ($KHSO_5$), particularly in the commercial product Oxone®. Oxone is a complex mixture of derivatives of sulfuric acid in which potassium peroxymonosulfate is the active reagent. It is preferably used in acetone, in which dimethyloxirane is formed in situ as an active oxidizing reagent.

Preferably, reducing methods for conversion of N-oxyamino and/or N-oxyimino intermediates to racemic primary amines are selected from catalytic hydrogenation on palladium catalyst on a supporter as a preferred catalyst or from reduction with metals form low oxidation states, such as $Fe^{2+}$, $Sn^{2+}$, elemental tin and zinc, most preferably elemental zinc in acidic medium is used.

According to a particularly preferred embodiment, the oxidizing agent is potassium peroxymonosulfate ($KHSO_5$) and/or the reducing agent is elemental zinc (Zn). Thereby, a particularly effective combination of oxidizing agent and reducing agent is selected. Although according to literature (J. Org Chem. 57, 6759 (1992)) potassium peroxymonosulfate in acetone may lead to a complex mixture of oxidation intermediates, it was surprisingly found that following by reduction with zinc in hydrochloric acid the intermediates are transformed to the unique compound of formula IV with high selectivity.

According to another preferred embodiment of the invention, in step i) and ii), pH of the reaction mixtures is suitably adjusted in view of the oxidizing and reducing agent respectively applied. Thus, using potassium peroxymonosulfate in acetone the pH value is adjusted to mild alkaline from 7 to 10, preferably 7 to 9, most preferably pH is 9 in the part of the reaction time. The preferred reagent for pH adjustment is the phosphate buffer and potassium hydroxide for alkalizing. The reduction with elemental zinc is carried out in highly acidic medium with pH lower than 4, preferably lower than 2, accomplished by preceding addition of mineral acid, preferably hydrochloric acid or acetic acid.

According to still another preferred embodiment of the invention, subsequent to step i) and prior to step ii), water and/or organic solvents are removed from the reaction mixture.

According to a particularly preferred embodiment, the oxidizing agent is potassium peroxymonosulfate ($KHSO_5$) and/or the reducing agent is elemental zinc (Zn).

According to another particularly preferred embodiment, compound of formula I is prepared via the above described enzymatic kinetic resolution process. In this way, a particularly desirable recycling concept is provided, since "undesired" enantiomer of compound of formula I can be converted to "desired" enantiomer of compound of formula I. That is, in a reaction affording an enantiomer which is undesired, for example in the above described enzymatic kinetic resolution process, the resulting undesired enantiomer can be recycled by converting it to the desired enantiomer. In particular, in said enzymatic kinetic resolution process, it is preferred that at least a part of the amount of compound of formula II is prepared according to the aforementioned racemisation process.

In another preferred embodiment of the invention, compound of formula II

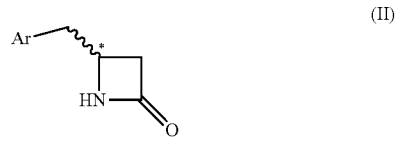

(II)

for the above-described coupling reaction and/or enzymatic kinetic resolution is prepared from a compound of formula I

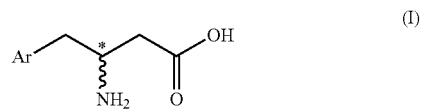

(I)

by means of a cyclodehydration reaction.

According to this preferred embodiment of the invention, a particularly advantageous procedural concept is provided which renders possible to recycle compound of formula I, preferably obtained by the aforementioned enzymatic kinetic resolution process, as compound of formula II in the coupling process according to item (1). In particular, it is preferred to cyclodehydrate compound of formula I in the form of its (substantially) enantiopure R-enantiomer to compound of formula II", since compound of formula II" in the form of its R-enantiomer represents a particularly advantageous starting material for the coupling process according to item (1).

Preferably, cyclodehydration of β-amino carboxylic acids to β-lactames is carried out by applying various dehydration reagents such as carbodiimides, preferably dicyclohexylcarbodiimide, triphenylphosphine in combination with tetrahalomethanes, with N-bromo compounds, such as N-bromosuccinimide, with oxalyl chloride in combination with N,N'-dimethylformamide (Vilsmeier reagent), or with disulfides or by transforming the acid to highly reactive derivatives such as acid chlorides or mixed anhydrides with phosphonic or sulfonic acids. More preferably cyclodehydration of β-amino carboxylic acids to β-lactames is carried out by applying a C1-C6-alkylsulfonyl chloride or arylsulfonyl chloride in combination with a proton acceptor which converted the mixed anhydride to β-lactames. Preferably methanesulfonyl chloride ($MeSO_2Cl$) and $NaHCO_3$ are applied as reactants. Thereby, a combination of reagents is selected which provides for particularly effective cyclodehydration reaction.

According to a preferred embodiment, compound of formula I applied as the starting material for cyclodehydration reaction is prepared according to the enzymatic kinetic resolution process described above. Preferably, the thus obtained compound of formula II is applied as the starting material in the coupling process described above. In this way, a further particularly desirable recycling concept is provided, since compound of formula I prepared by the aforementioned racemisation process and/or enzymatic kinetic resolution process can be converted to compound of formula II, which in turn can be applied as the starting material in the coupling process described above.

According to another aspect of the invention, a process for the preparation of a pharmaceutical composition comprising compound of formula IV or a pharmaceutically acceptable salt thereof as pharmaceutically active ingredient is provided, the process comprises the steps of:

a) preparing a compound of formula IV or a salt thereof according to the process according to any one of items (1) to (15), (17) to (26), (34) and (39), and
b) admixing the prepared compound of formula IV or pharmaceutically acceptable salt thereof with at least one pharmaceutically acceptable excipient.

The term "pharmaceutically acceptable excipient" as used herein means any physiologically inert, pharmacologically inactive material known in the art being compatible with the physical and chemical characteristics of the active agent. Preferably, the pharmaceutically acceptable excipient is selected from the group consisting of binders, disintegrants, bulk polymers and preservatives.

The term "binder" as used herein means a binding agent which improves adhesion in between particles of the pharmaceutically active agent.

The term "disintegrant" as used herein means an agent providing for rapid disintegration of a pharmaceutical composition into smaller fragments when in contact with water, wherein dissolution of the pharmaceutical composition and in particular of a pharmaceutically active agent comprised therein is improved.

The term "bulk polymer" as used herein means a polymeric filling agent which is typically added to a pharmaceutical composition in large amounts, at least in an amount larger than 6% by weight relative to the total weight of the pharmaceutical composition.

The term "preservatives" as used herein means a substance or mixture of substances which prevents decomposition of a pharmaceutical composition, e.g. microbial or bacterial decomposition.

According to a preferred embodiment, in the pharmaceutical composition, compound of formula IV is sitagliptin having the structural formula,

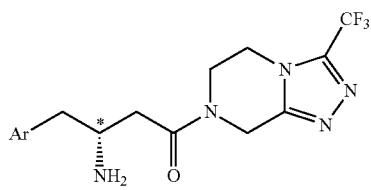

preferably sitagliptin is in the form of its phosphate salt.

According to another preferred embodiment, the pharmaceutical composition comprises at least one additional pharmaceutically active ingredient besides of compound of formula IV, wherein said additional pharmaceutically active ingredient is selected from the group consisting of insulin sensitizers, insulin, insulin mimetics, sulfonylureas, (glucosidase inhibitors, glucagon receptor antagonists, GLP-1, GLP-1 analogues, GLP-1 mimetics, GLP-1 receptor agonists, GIP, GIP mimetics, PACAP, PACAP mimetics, PACAP receptor agonists, cholesterol lowering agents, PPAR-δ agonists, anti-obesity compounds, ileal bile acid transporter inhibitors, agents intended for use in inflammatory conditions, antihypertensive agents, glucokinase activators (GKAs), inhibitors of 11(-hydroxysteroid dehydrogenase type 1, inhibitors of cholesteryl ester transfer protein (CETP) and inhibitors of fructose 1,6-bisphosphatase. Preferably, the additional pharmaceutically active ingredient is metformin and/or its pharmaceutically acceptable salt.

The following examples are merely illustrative of the present invention and they should not be considered as limiting the scope of the invention in any way. The examples and modifications or other equivalents thereof will become apparent to those versed in the art in the light of the present entire disclosure.

EXAMPLES

Example 1

Racemic 3-amino-4-(2,4,5-trifluorophenyl)butanoic acid (Ia)

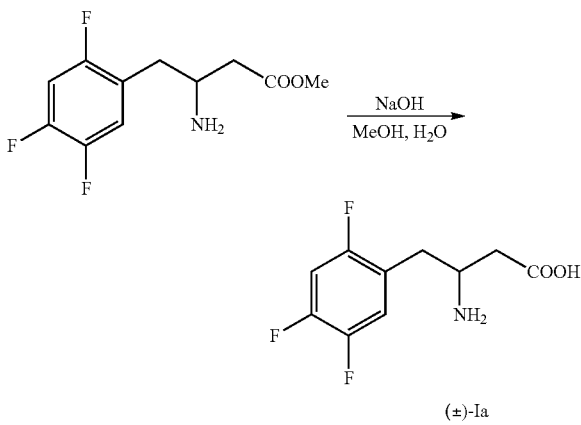

Methyl 3-amino-4-(2,4,5-trifluorophenyl)butanoate (5.8 g, 23.5 mmol), prepared from methyl 3-oxo-4-(2,4,5-trifluorophenyl)butanoate according to the process of WO 10/122578, was refluxed in the solution of NaOH (1.88 g, 46.9 mmol) in MeOH (40 mL) and water (20 mL) overnight. After the completion of the reaction, the MeOH was evaporated and 80 mL of water was added. The pH of the solution was adjusted to 8 by addition of 6M HCl and the resulting white precipitate was filtered off and dried overnight in an oven at 100° C. to afford 3.5 g of (±)-Ia.

Example 2

Racemic 4-(2,4,5-trifluorobenzyl)azetidin-2-one ((±)-IIa)

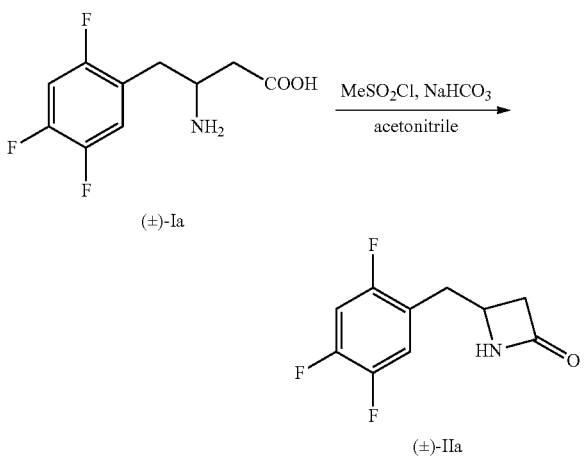

To the rapidly stirred 80° C. suspension of methanesulfonyl chloride (0.88 g, 7.72 mmol) and sodium bicarbonate (3.24 g, 38.6 mmol) in acetonitrile (400 mL), 3-amino-4-(2,4,5-trifluorophenyl)butanoic acid ((±)-Ia, 1.5 g, 6.43 mmol) is added over period of 2 h. The resulting suspension was further stirred for 16 h at 80° C., after which time the fine suspension was cooled to 0° C. and filtered. The filtrate was evaporated under reduced pressure to afford 1.34 g (96% yield) of racemic 4-(2,4,5-trifluorobenzyl)azetidin-2-one ((±)-IIa) as pale yellow crystalline solid.

Example 3

(R)-4-(2,4,5-trifluorobenzyl)azetidin-2-one (IIa″) and (S)-3-amino-4-(2,4,5-trifluorophenyl)butanoic acid ((S)-Ia′)

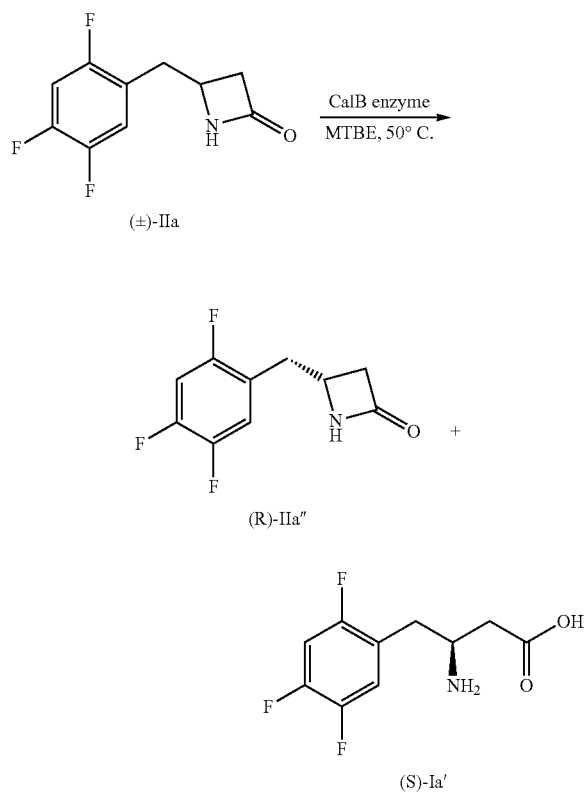

To a suspension of racemic 4-(2,4,5-trifluorobenzyl)azetidin-2-one ((±)-IIa) (50 mg, 0.23 mmol) in MTBE (15.0 mL) was added *Candida antarctica* lipase B (CalB) enzyme in recombinant form immobilised on polyacryllic resin (375 mg), and the mixture was mixed for 40 h at 50° C. After the separation of the enzyme beads from the rest of the mixture by filtration through 0.1 mm filter net, the remaining suspension was filtrated through 0.22 μm teflon filter and washed two times with 2×5 mL of MTBE. The remaining white solid was collected and re-suspended in cold acetonitrile (2 mL), filtered off and dried to afford 24 mg of (S)-Ia′ as white amorphous solid (ee 97%). The MTBE filtrate was evaporated to afford 18 mg of compound (R)-IIa″ as white crystals (ee 99%).

Example 4

Racemic 3-amino-4-(2,4,5-trifluorophenyl)butanoic acid ((±)-Ia)

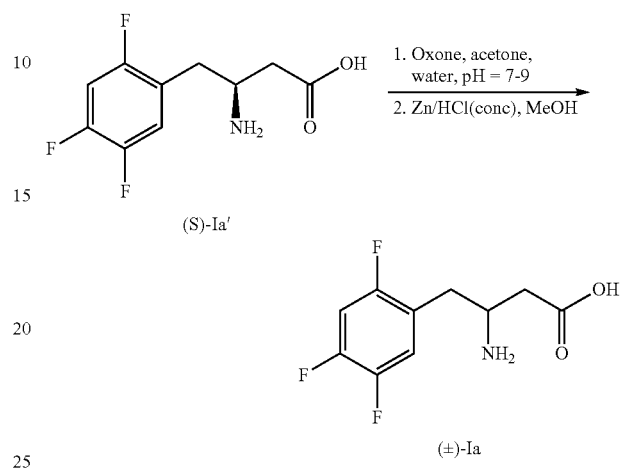

To the suspension of (S)-Ia′ (2.0 g, 8.58 mmol) in acetone (35 ml) and 0.1 M phosphate buffer (35 mL), the solution of Oxone® (15.8 g, 25.7 mmol) in water (20 mL) was added slowly over period of 20 min at 5° C. The pH 7-8 was maintained by addition of 5M KOH. After all Oxone® was added and pH stabilized at 8.0 the mixture was allowed to warm to room temperature. After 1 h the pH of the reaction mixture was elevated to 9.0 and the mixture was stirred for 16 hours at room temperature. Then the acetone was evaporated in vacuum and the pH of remaining water suspension was lowered to 2.0 and washed with EtOAc (80 mL). After the removal of water phase, the organic phase was dried over MgSO₄, filtered and evaporated in vacuum. The remaining yellow oily residue (1.9 g) was dissolved in 120 mL of MeOH and cooled to 0° C. Powdered Zn (12 g) and 36% HCl (10 mL) were added and after 1 h the mixture was allowed to stir at room temperature for further 16 h. Zinc particles were removed by filtration and methanol was removed under reduced pressure. To the remaining oily residue, water was added and pH elevated to 8. The precipitated white solid was filtered off and dried in an oven to afford 1.9 g of (±)-Ia.

Example 5

(R)-3-amino-1-(3-(trifluoromethyl)-5,6-dihydro-[1,2,4]triazolo[4,3-a]pyrazin-7(8H)-yl)-4-(2,4,5-trifluorophenyl)butan-1-one (sitagliptin) (IV)

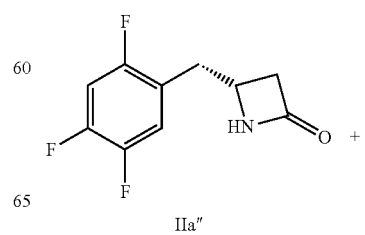

-continued

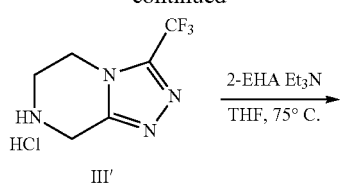

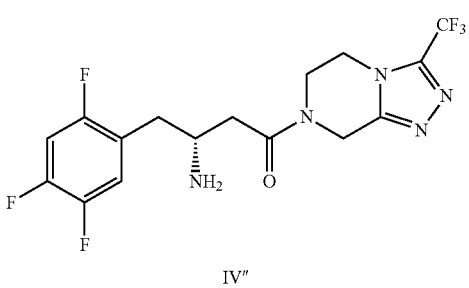

Azetidinone IIa' (0.5 g, 2.32 mmol, ee 99.5%), 3-(trifluoromethyl)-5,6,7,8-tetrahydro-[1,2,4]triazolo[4,3-a]pyrazine hydrochloride (III',1.06 g, 4.65 mmol), Et₃N (0.28 g, 4.65 mmol) and 2-ethylhexanoic acid (0.17 g, 1.16 mmol) were suspended in THF (10 mL). The resulting suspension was stirred at 75° C. for 72 h. After cooling the mixture to 0° C., the excess of the compound III' was filtered off and the solvent was removed in vacuo. To the remaining oil was added water (10 mL) and the product was extracted with dichloromethane (3×10 mL). The organic phases were combined, dried over magnesium sulfate and concentrated in vacuo to give 0.90 g of sitagliptin (IV") (95%, ee 99.5%) as dark yellow oil.

Example 6

(R)-3-amino-1-(3-(trifluoromethyl)-5,6-dihydro-[1,2,4]triazolo[4,3-a]pyrazin-7(8H)-yl)-4-(2,4,5-trifluoro phenyl)butan-1-one (sitagliptin) (IV)

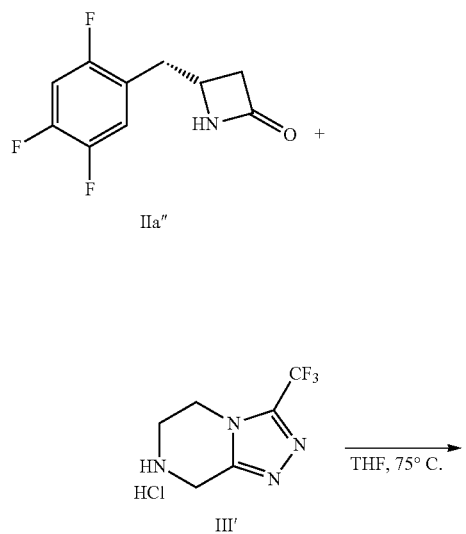

-continued

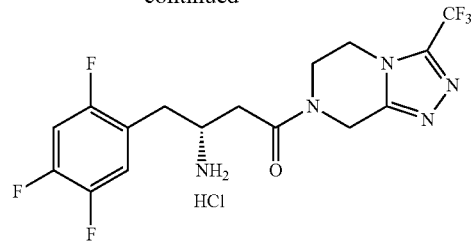

Azetidinone IIa' (2.24 g, 10.4 mmol, ee 99.5%) and 3-(trifluoromethyl)-5,6,7,8-tetrahydro-[1,2,4]triazolo[4,3-a]pyrazine hydrochloride III'(2.38 g, 10.4 mmol) were suspended in THF (30 mL). The resulting mixture was stirred and heated under reflux for 18 h. The reverse phase HPLC showed full conversion of starting material compared to reference sitagliptin standard and the suspension was cooled to 25° C. The white precipitate was filtered off, washed with THF and dried in vacuo to afford 4.2 g of sitagliptin (IV") hydrochloride (90%, ee 99.5%). ¹H NMR (DMSO-D₆): δ 2.75-3.14 (m, 4H), 3.64-4.34 (m, 5H), 4.79-5.02 (m, 2H), 7.48-7.63 (m, 2H), 8.32 (s, 3H, NH₃) ppm.

Example 7

(R)-3-amino-1-(3-(trifluoromethyl)-5,6-dihydro-[1,2,4]triazolo[4,3-a]pyrazin-7(8H)-yl)-4-(2,4,5-trifluoro phenyl)butan-1-one (Sitagliptin) (IV)

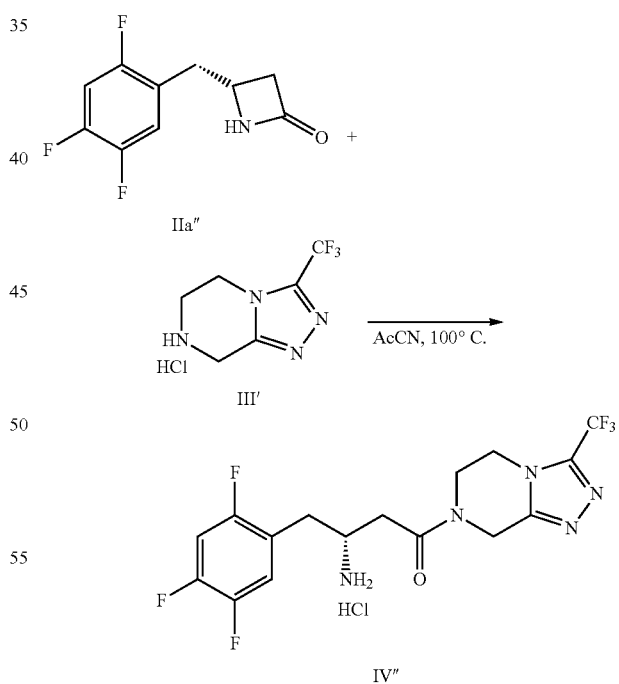

Azetidinone IIa' (0.10 g, 0.46 mmol, ee 99.5%) and 3-(trifluoromethyl)-5,6,7,8-tetrahydro-[1,2,4]triazolo[4,3-a]pyrazine hydrochloride III'(0.11 g, 0.46 mmol) were dissolved in AcCN (2 mL). The reaction mixture was stirred at 100° C. in a high pressure vial and monitored by rp HPLC. After 2 h, the full HPLC conversion was observed and the solvent was evaporated to afford 0.190 g of sitagliptin hydrochloride (IV") as a white foamy solid (92%, ee 99.5%).

Example 8

(R)-3-amino-1-(3-(trifluoromethyl)-5,6-dihydro-[1,2,4]triazolo[4,3-a]pyrazin-7(8H)-yl)-4-(2,4,5-trifluorophenyl)butan-1-one (Sitagliptin) (IV)

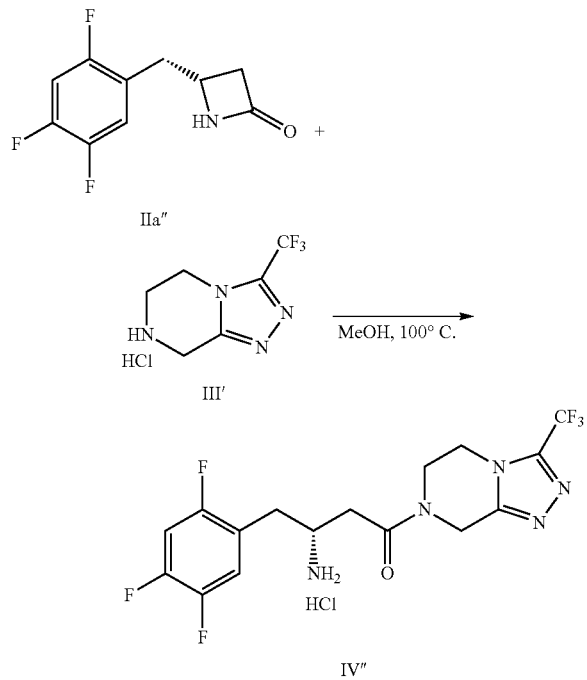

Azetidinone IIa' (0.10 g, 0.46 mmol, ee 99.5%) and 3-(trifluoromethyl)-5,6,7,8-tetrahydro-[1,2,4]triazolo[4,3-a]pyrazine hydrochloride III'(0.11 g, 0.46 mmol) were dissolved in MeOH (2 mL). The reaction mixture was stirred at 100° C. in a high pressure vial and monitored by rp HPLC. After 18 h, the full conversion was observed and the solvent was evaporated to afford 0.170 g of sitagliptin hydrochloride (IV") as a white foamy solid (83%, ee 99.5%).

Example 9

(R)-3-amino-1-(3-(trifluoromethyl)-5,6-dihydro-[1,2,4]triazolo[4,3-a]pyrazin-7(8H)-yl)-4-(2,4,5-trifluorophenyl)butan-1-one (Sitagliptin) (IV)

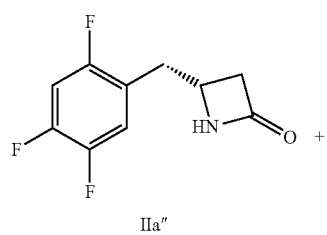

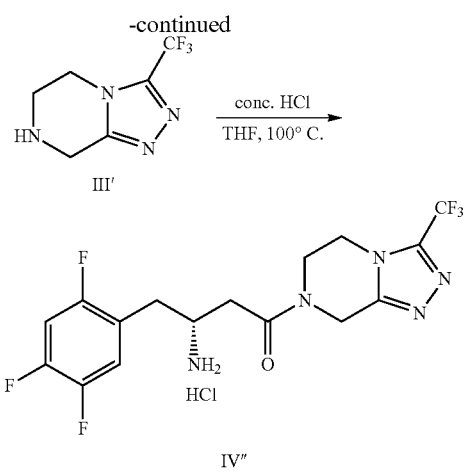

Azetidinone IIa' (0.10 g, 0.46 mmol, ee 99.5%) and 3-(trifluoromethyl)-5,6,7,8-tetrahydro-[1,2,4]triazolo[4,3-a]pyrazine III'(0.09 g, 0.46 mmol) were dissolved in THF (2 mL). After the addition of 0.04 mL of concentrated (37%) HCl, the reaction mixture was stirred at 100° C. in a high pressure vial and monitored by HPLC. After 20 h, the full conversion was observed by rp HPLC and the reaction was cooled to 25° C. The white precipitate was filtered off and dried to afford 0.185 g of sitagliptin hydrochloride (IV") (90%, ee 99.5%).

Example 10

(R)-3-amino-1-(3-(trifluoromethyl)-5,6-dihydro-[1,2,4]triazolo[4,3-a]pyrazin-7(8H)-yl)-4-(2,4,5-trifluorophenyl)butan-1-one (Sitagliptin) (IV)

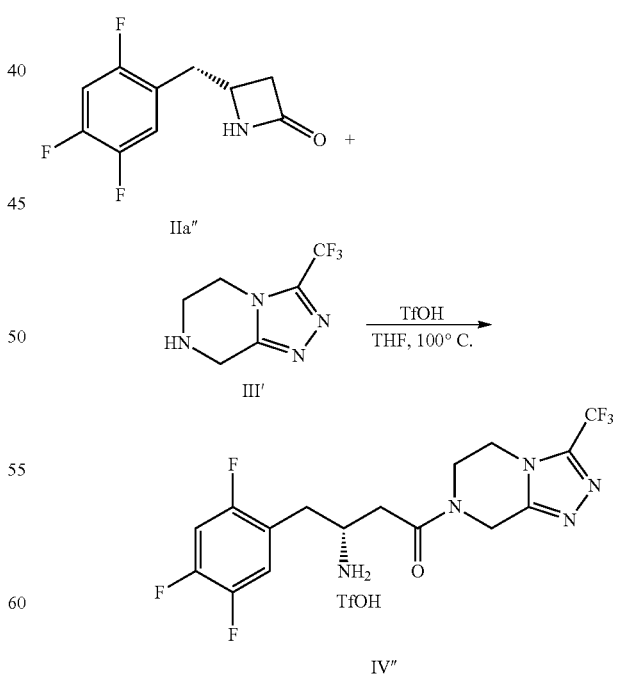

Azetidinone IIa' (0.10 g, 0.46 mmol, ee 99.5%) and 3-(trifluoromethyl)-5,6,7,8-tetrahydro-[1,2,4]triazolo[4,3-a]pyrazine (III', 0.09 g, 0.46 mmol) were dissolved in THF (2 mL).

After the addition of trifluoromethanesulfonic acid (0.07 g, 0.46 mmol), the reaction mixture was stirred at 100° C. in a high pressure vial. After 16 h, the full conversion was observed by rp HPLC compared to reference sitagliptin standard.

Example 11

(R)-3-amino-1-(3-(trifluoromethyl)-5,6-dihydro-[1,2,4]triazolo[4,3-a]pyrazin-7(8H)-yl)-4-(2,4,5-trifluorophenyl)butan-1-one (Sitagliptin) (IV)

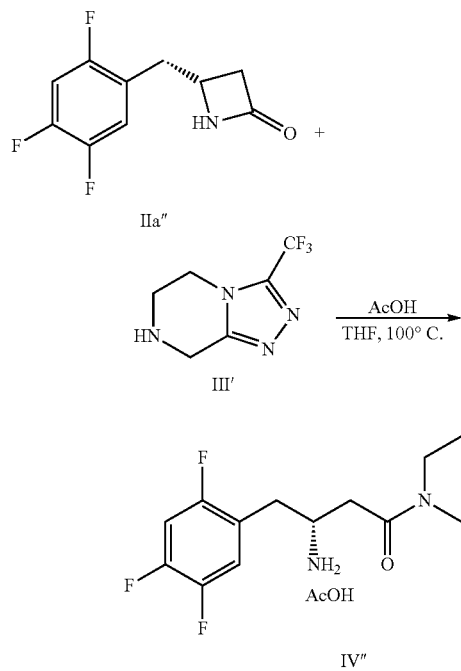

Azetidinone IIa' (0.10 g, 0.46 mmol, ee 99.5%) and 3-(trifluoromethyl)-5,6,7,8-tetrahydro-[1,2,4]triazolo[4,3-a]pyrazine (III', 0.09 g, 0.46 mmol) were dissolved in THF (2 mL). After the addition of acetic acid (0.03 g, 0.46 mmol), the reaction mixture was stirred at 100° C. in a high pressure vial. After 16 h, the full conversion was observed by rp HPLC compared to reference sitagliptin standard.

Example 12

(R)-3-amino-1-(3-(trifluoromethyl)-5,6-dihydro-[1,2,4]triazolo[4,3-a]pyrazin-7(8H)-yl)-4-(2,4,5-trifluorophenyl)butan-1-one (Sitagliptin) (IV)

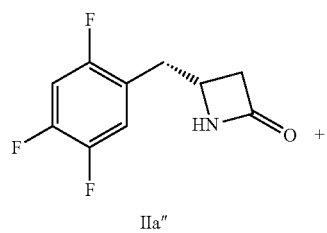

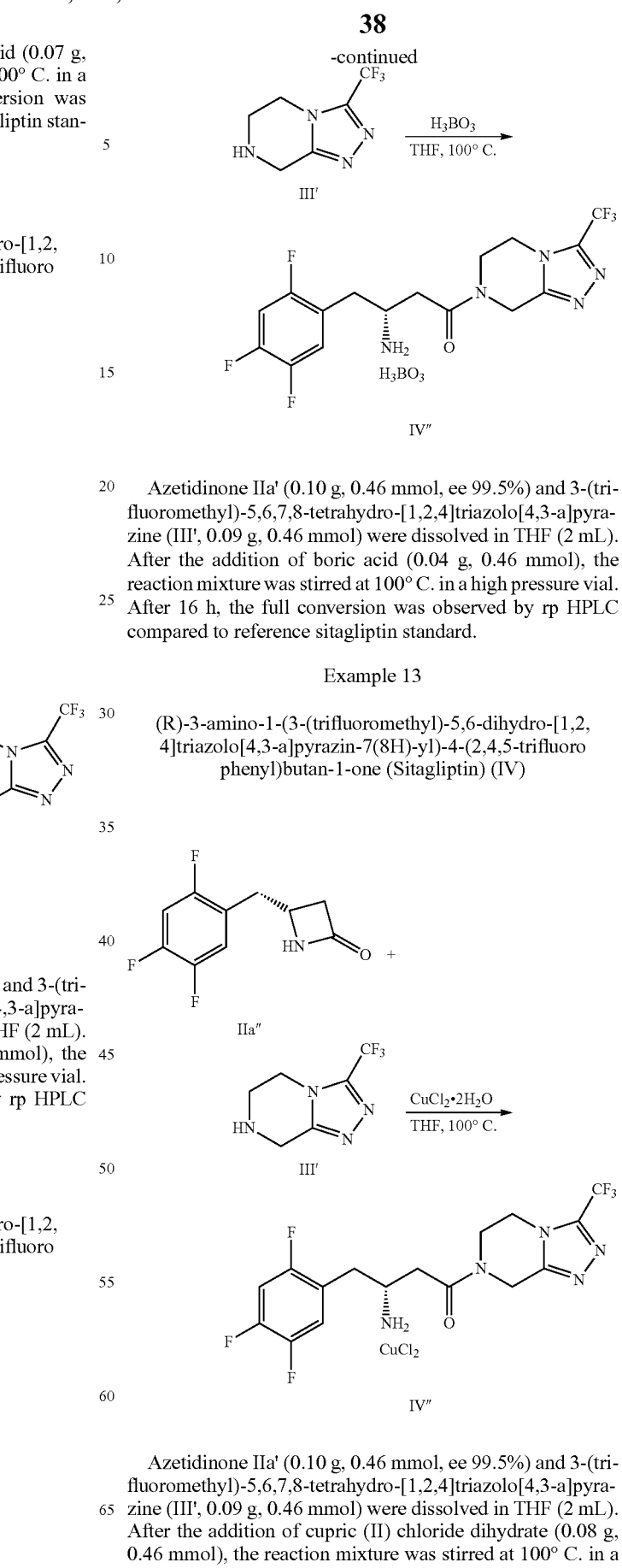

Azetidinone IIa' (0.10 g, 0.46 mmol, ee 99.5%) and 3-(trifluoromethyl)-5,6,7,8-tetrahydro-[1,2,4]triazolo[4,3-a]pyrazine (III', 0.09 g, 0.46 mmol) were dissolved in THF (2 mL). After the addition of boric acid (0.04 g, 0.46 mmol), the reaction mixture was stirred at 100° C. in a high pressure vial. After 16 h, the full conversion was observed by rp HPLC compared to reference sitagliptin standard.

Example 13

(R)-3-amino-1-(3-(trifluoromethyl)-5,6-dihydro-[1,2,4]triazolo[4,3-a]pyrazin-7(8H)-yl)-4-(2,4,5-trifluorophenyl)butan-1-one (Sitagliptin) (IV)

Azetidinone IIa' (0.10 g, 0.46 mmol, ee 99.5%) and 3-(trifluoromethyl)-5,6,7,8-tetrahydro-[1,2,4]triazolo[4,3-a]pyrazine (III', 0.09 g, 0.46 mmol) were dissolved in THF (2 mL). After the addition of cupric (II) chloride dihydrate (0.08 g, 0.46 mmol), the reaction mixture was stirred at 100° C. in a high pressure vial. After 16 h, the full conversion was observed by rp HPLC compared to reference sitagliptin standard and the solvent was evaporated in vacuo. The green oily residue was partitioned between EtOAc and 1 M aqueous solution of NaOH. The aqueous layer was extracted with EtOAc three times. The combined organic phases were washed with brine, dried over anhydrous sodium sulfate and concentrated in vacuo. The yellow residue was dissolved in 2 mL of the saturated methanolic HCl and stirred for 10 min at 25° C. for 1 h. The concentration in vacuo afforded hydrochloric salt of sitagliptin as a white foam (150 mg, 74%, ee 99.5%).

Example 14

(R)-3-amino-1-(3-(trifluoromethyl)-5,6-dihydro-[1,2,4]triazolo[4,3-a]pyrazin-7(8H)-yl)-4-(2,4,5-trifluoro phenyl)butan-1-one (Sitagliptin) (IV)

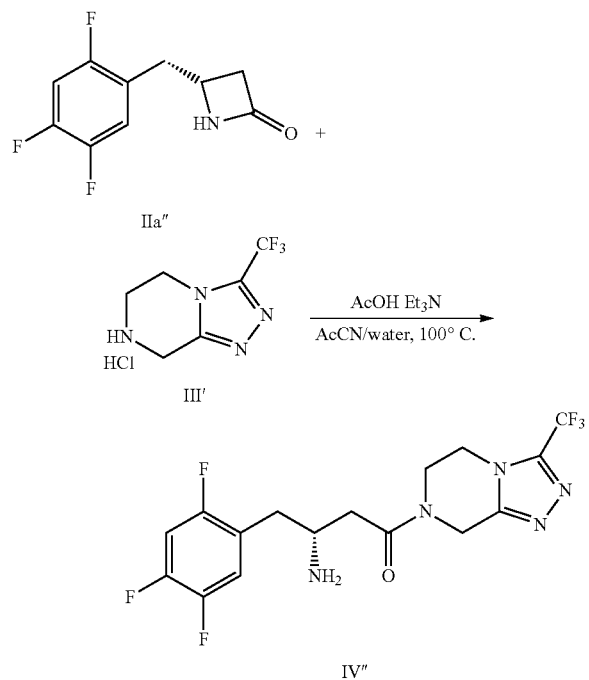

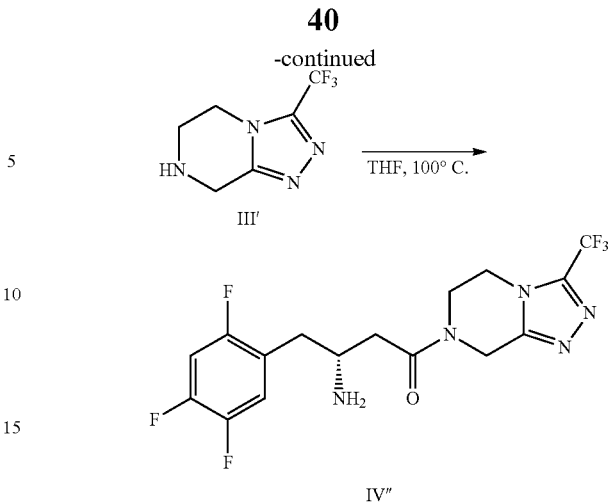

Azetidinone IIa' (0.10 g, 0.46 mmol, ee 99.5%), 3-(trifluoromethyl)-5,6,7,8-tetrahydro-[1,2,4]triazolo[4,3-a]pyrazine hydrochloride III' (0.212 g, 0.93 mmol), Et₃N (0.094 g, 0.93 mmol) were dissolved in 2 mL of AcCN/water mixture (1:1). After the addition of acetic acid (0.033 g, 0.23 mmol), the reaction mixture was stirred at 100° C. in a high pressure vial. After 16 h, the full conversion was observed by rp HPLC compared to reference sitagliptin standard.

Example 15

(R)-3-amino-1-(3-(trifluoromethyl)-5,6-dihydro-[1,2,4]triazolo[4,3-a]pyrazin-7(8H)-yl)-4-(2,4,5-trifluoro phenyl)butan-1-one (Sitagliptin) (IV)

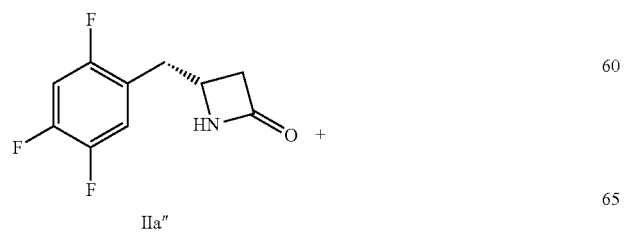

Azetidinone IIa' (0.10 g, 0.46 mmol, ee 99.5%) and 3-(trifluoromethyl)-5,6,7,8-tetrahydro-[1,2,4]triazolo[4,3-a]pyrazine (III', 0.09 g, 0.46 mmol) were dissolved in THF (2 mL) and the reaction mixture was stirred at 100° C. in a high pressure vial. After 20 h, the 20% conversion was observed by rp HPLC compared to reference sitagliptin standard.

Example 16

(R)-3-amino-1-(3-(trifluoromethyl)-5,6-dihydro-[1,2,4]triazolo[4,3-a]pyrazin-7(8H)-yl)-4-(2,4,5-trifluoro phenyl)butan-1-one (Sitagliptin) (IV)

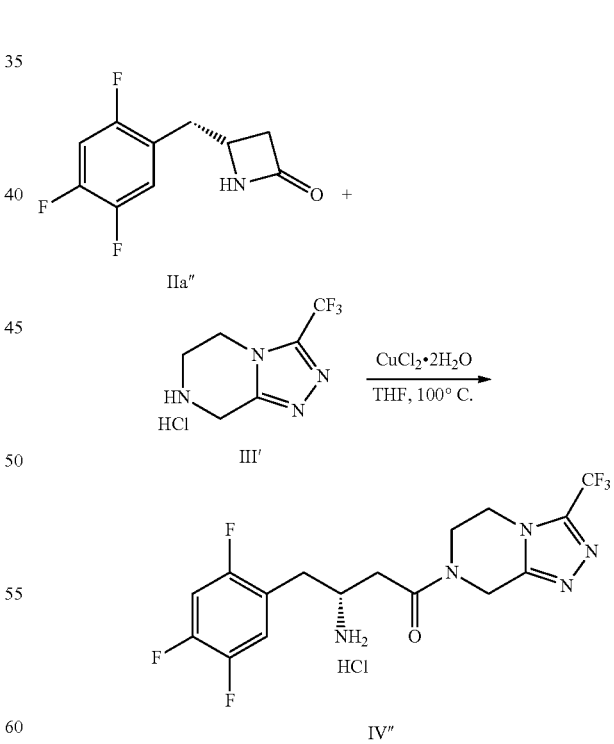

Azetidinone IIa' (0.10 g, 0.46 mmol, ee 99.5%) and 3-(trifluoromethyl)-5,6,7,8-tetrahydro-[1,2,4]triazolo[4,3-a]pyrazine hydrochloride III' (0.11 g, 0.46 mmol) were dissolved in THF (2 mL). After the addition of cupric (II) chloride dihydrate (0.008 g, 0.046 mmol), the reaction mixture was stirred at 100° C. in a high pressure vial. After 15 h, the full HPLC conversion was observed compared to reference sitagliptin standard.

The invention claimed is:

1. A process for the preparation of a compound of formula IV,

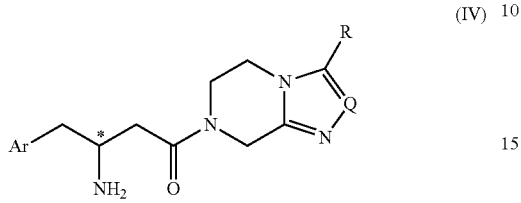

wherein Ar denotes unsubstituted or substituted C6-C12-aryl, Q denotes N, CH or a carbon substituted with unsubstituted or substituted C1-C6-alkyl, C6-C12-aryl or C7-C12-alkylaryl, and R denotes H or unsubstituted or substituted C1-C6-alkyl, C6-C12-aryl or C7-C12-alkylaryl, comprising a step of coupling a compound of formula II,

wherein Ar is defined as above,
with a compound of formula III or a salt thereof,

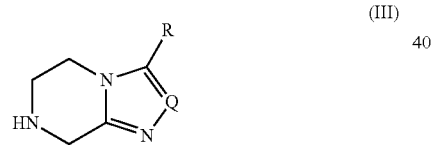

wherein R and Q are defined as above,
in the presence of a catalyst in an organic solvent.

2. The process according to claim 1, wherein the compound of formula II, III and/or IV is/are characterized by either one or a combination of the following features i) to vi):
i) the chiral center of compound of formula II and IV is in R-configuration;
ii) in compounds of formulae II and IV, Ar is substituted phenyl;
iii) in compounds of formula IV, R is substituted C1-C3-alkyl;
iv) in compounds of formula IV, Q is N;
v) Ar is 2,4,5-trifluorophenyl in the compounds of formulae II and IV, R is trifluoromethyl in the compounds of formulae III and IV, Q is N in the compounds of formulae III and IV and the chiral center is in R-configuration;
vi) compound of formula III is provided in the form of its acid addition salt.

3. The process according to claim 1, characterized by either one or a combination of procedural features I) to III):
I) the solvent is selected from the group of C2-C8 aliphatic ethers, C4-C6 cyclic ethers, C1-C4-alkyl C1-C4-alkanoates, aliphatic nitriles, C1-C2-alkanamides, dimethylsulfoxide, and C1-C4-alcohols;
II) the catalyst is selected from Broensted or Lewis acids, wherein the Broensted acid is selected from inorganic acids and organic acids selected from C1-C12-alkanecarboxylic acid, and unsubstituted or fluoro substituted C1-C4-alkanesulfonic acids, and wherein the Lewis acid is selected from iron, zinc, or copper salts,
III) in case compound of formula III is provided in the form of its acid addition salt the Broensted acid is applied in a form of an addition salt with the compound of formula III.

4. The process according to any claim 1, wherein the compound of formula II,

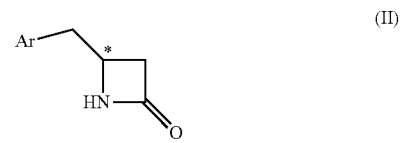

wherein Ar denotes unsubstituted or substituted C6-C12-aryl,
is provided in substantially enantiopure form; wherein the substantially enantiopure compound is a compound of formula II' or II'' having the structural formula

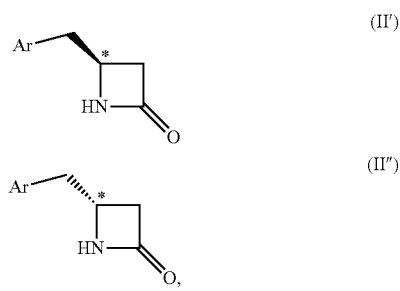

wherein Ar is defined as above,
which is prepared by subjecting racemic or enantioenriched compound of formula II,

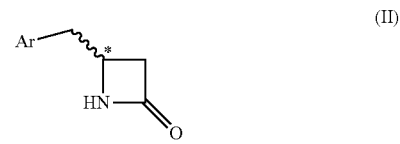

wherein Ar is defined as above,
to kinetic resolution by means of a hydrolytic enzyme in the presence of an organic solvent, wherein one kind of enantiomer of compound of formula II is converted to a compound of formula I,

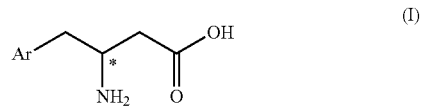

wherein Ar is defined as above,
while the other enantiomer of compound of formula II remains substantially unreacted.

5. The process according to claim 4, wherein the S-enantiomer of compound of formula II is converted to compound of formula I, while the R-enantiomer of compound of formula II remains substantially unreacted.

6. The process according to claim 4, characterized by either one or a combination of the features a) to g):
   a) compound of formula II provided as the starting material is in racemic form;
   b) the hydrolytic enzyme is selected from the group of lipases;
   c) the process is carried out at the temperature from 25° C. to 70° C.;
   d) the enzyme is immobilised on a polymer resin;
   e) compound of formula II" or IIa" obtained after enzymatic racemic resolution has an enantiomeric excess (ee) of at least 80%;
   f) the organic solvent is selected from C5-C7 alkanes, C2-C8 aliphatic ethers, C4-C6 cyclic ethers, C1-C4-alkyl C1-C4-carboxylates and C1-C4-alcohols and toluene;
   g) the hydrolytic enzyme is removed and subsequently the compound of formula I is separated from the resulting reaction mixture by filtration, centrifugation, or decantation.

7. The process according to claim 1, wherein compound of formula II

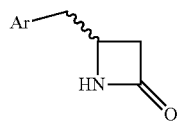

is prepared from compound of formula I

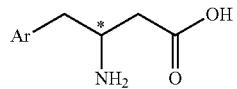

by means of a cyclodehydration reaction.

8. The process according to claim 7, wherein cyclodehydration is carried out by applying C1-C6-alkanesulfonyl chloride, or arylsulfonyl chloride and a proton acceptor as reactants.

9. The process according to claim 1, for a preparation of a compound of formula IV in (R) configuration, wherein the compound of formula II is prepared by the following steps:

1) providing an S-enantiomer of compound of formula I,

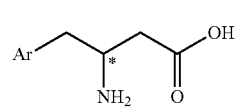

wherein Ar denotes unsubstituted or substituted C6-C12-aryl, 2) racemizing the compound of step 1) by
   i) oxidation of the S-enantiomer of the compound of formula I to its C—N double bonded intermediates by means of an oxidizing agent, and
   ii) reduction of the C—N double bonded intermediates obtained in step i) by means of a reducing agent, in order to obtain the compound of formual I in racemic form; and 3) submitting the racemic compound of step 2) to a cyclodehydration reaction to form the compound of formula II

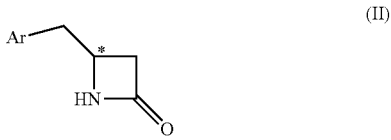

wherein Ar is defined as above.

10. A process for the preparation of a pharmaceutical composition comprising compound of formula IV or a pharmaceutically acceptable salt thereof as pharmaceutically active ingredient, comprising the steps of:
   a) preparing a compound of formula IV or a salt thereof according to the process according to claim 1, and
   b) admixing the prepared compound of formula IV or pharmaceutically acceptable salt thereof with at least one pharmaceutically acceptable excipient.

11. The process according to claim 9, wherein compound of formula IV is sitagliptin having the structural formula

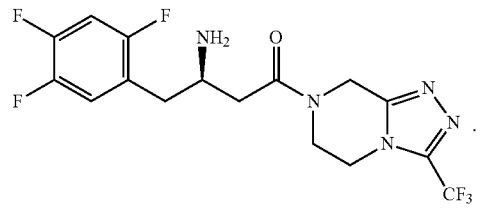 [SMILES: N[C@@H](CC(=O)N1CCn2c(nnc2C(F)(F)F)C1)Cc1cc(F)c(F)cc1F]

* * * * *